United States Patent
Lenhard et al.

(10) Patent No.: US 6,498,004 B1
(45) Date of Patent: Dec. 24, 2002

(54) SILVER HALIDE LIGHT SENSITIVE EMULSION LAYER HAVING ENHANCED PHOTOGRAPHIC SENSITIVITY

(75) Inventors: Jerome R. Lenhard, Fairport, NY (US); Annabel A. Muenter, Rochester, NY (US); Stephen A. Godleski, Fairport, NY (US); Paul A. Zielinski, Rochester, NY (US); Deepak Shukla, Webster, NY (US); Donald R. Diehl, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/750,855

(22) Filed: Dec. 28, 2000

(51) Int. Cl.$^7$ .................................. G03C 1/08
(52) U.S. Cl. ............... 430/583; 430/544; 430/546; 430/570; 430/572; 430/581; 430/599; 430/600; 430/607; 430/611; 430/613; 548/477; 548/546; 548/251; 548/544; 548/156; 548/261; 548/210; 558/394; 560/29; 560/43; 562/452
(58) Field of Search ................ 430/544, 546, 430/581, 583, 599, 600, 570, 572, 607, 611, 613; 548/477, 546, 251, 544, 156, 261, 210; 558/394; 560/29, 43; 562/452

(56) References Cited

U.S. PATENT DOCUMENTS

| | | |
|---|---|---|
| 4,146,396 A | 3/1979 | Yokota et al. |
| 4,248,962 A | 2/1981 | Lau |
| 4,409,323 A | 10/1983 | Sato et al. |
| 4,421,845 A | 12/1983 | Uemura et al. |
| 4,428,962 A | 1/1984 | Bristol et al. |
| 4,546,073 A | 10/1985 | Bergthaller et al. |
| 4,652,516 A | 3/1987 | Ichijima et al. |
| 4,698,297 A | 10/1987 | Ichijima et al. |
| 4,772,537 A | 9/1988 | Itoh et al. |
| 5,019,492 A | 5/1991 | Buchanan et al. |
| 5,256,525 A | 10/1993 | Southby et al. |
| 5,302,498 A | 4/1994 | Southby et al. |
| 5,747,235 A | 5/1998 | Farid et al. |
| 5,747,236 A | 5/1998 | Farid et al. |
| 5,830,625 A | 11/1998 | Hirano |
| 5,994,051 A | 11/1999 | Gould et al. |
| 6,010,841 A | 1/2000 | Farid et al. |
| 6,054,260 A | 4/2000 | Adin et al. |
| 6,153,371 A | 11/2000 | Farid et al. |

FOREIGN PATENT DOCUMENTS

| | | |
|---|---|---|
| GB | 2096783 | 7/1979 |
| GB | 1531927 | 3/1998 |
| JP | 57 56837 | 4/1982 |

OTHER PUBLICATIONS

Abstract: DE 3518797.
Abstract: DE 3518231.
Abstract: JP 57056837.
Abstract: DE 2626315.
Abstract: GB 2096783.

*Primary Examiner*—Janet Baxter
*Assistant Examiner*—Amanda C. Walke
(74) *Attorney, Agent, or Firm*—Edith A. Rice; Sarah Meeks Roberts

(57) ABSTRACT

This invention provides a photographic element comprising at least one silver halide emulsion layer in which the silver halide is sensitized with a compound of the formula (a):

$$\Delta-(t)_m-XY' \qquad (a)$$

$$XY'-(t)_m-\Delta \qquad (b)$$

$$\Delta-(t)_m-XY'-(t)_m-\Delta \qquad (c)$$

wherein $\Delta$ is protective group that is eliminated during development of the photographic element, t is a timing group, m is an integer from 0 to 3, and XY' is a fragmentable electron donor moiety in which X is an electron donor group and Y' is a leaving proton H or a leaving group Y, with the proviso that if Y' is a proton, a base, $\beta^-$, is present in the emulsion or is covalently linked directly or indirectly to X, and wherein:

1) X—Y' has an oxidation potential between 0 and about 1.4 V;
2) the oxidized form of X—Y' undergoes a bond cleavage reaction to give the radical X$^\bullet$ and the leaving fragment Y', and
3) the radical X$^\bullet$ has an oxidation potential $\leq -0.7$V.

37 Claims, No Drawings

SILVER HALIDE LIGHT SENSITIVE EMULSION LAYER HAVING ENHANCED PHOTOGRAPHIC SENSITIVITY

FIELD OF THE INVENTION

This invention relates to a photographic element comprising at least one light sensitive silver halide emulsion layer which has enhanced photographic sensitivity.

BACKGROUND OF THE INVENTION

The use of fragmentable electron donor (FED) compounds to enhance the sensitivity of silver halide emulsions has been demonstrated to be quite effective. The FED compounds have been proven to provide a sensitizing effect alone or in combination with spectral sensitizing dyes. Fragmentable electron donating compounds are described in U.S. Pat. Nos. 5,747,235 and 5,747,236 and 5,994,051, 6,010,841, 6,054,260 and 6,153,371, the entire disclosures thereof are incorporated herein by reference. These FED compounds can donate two electrons and are fragmentable, i.e., they undergo a bond cleavage reaction.

PROBLEM TO BE SOLVED BY THE INVENTION

While the use of fragmentable two-electron donors increases the speed of the emulsions disclosed in the above mentioned patents, these speed increases are sometimes accompanied by unwanted fogging of the emulsion. It is desirable to have silver halides sensitized with FEDs without an increase in fog. SUMMARY OF THE INVENTION We have now discovered that compounds that release fragmentable electron donors can improve sensitivity of photographic emulsions. In this application we describe fragmentable two-electron donor compounds that are attached to a protective group wherein such protective group is eliminated during development to give the fragmentable electron donor. The protected FED is effectively inert during the preparation, coating, and storage but becomes activated during processing of the photographic element. It is desirable to attach such a protective group to the FED so that the beneficial sensitizing effects can be obtained with lower amounts of unwanted fog.

In accordance with this invention, a silver halide emulsion layer of a photographic element is sensitized with a compound that releases a fragmentable electron donor moiety that upon donating an electron, undergoes a bond cleavage reaction to give a reducing radical. The term "sensitization" is used in this patent application to mean an increase in the photographic response of the silver halide emulsion layer of a photographic element. The term "sensitizer" is used to mean a compound that provides sensitization when present in a silver halide emulsion layer.

One aspect of this invention comprises a photographic element comprising at least one silver halide emulsion layer in which the silver halide is sensitized with a compound of the formula (a), (b) or (c):

 (a)

 (b)

 (c)

wherein Δ is protective group that is eliminated during development of the photographic element, t is a timing group, m is an integer from 0 to 3, and XY' is a fragmentable electron donor moiety in which X is an electron donor group and Y' is a leaving proton H or a leaving group Y, with the proviso that if Y' is a proton, a base, β⁻, is present in the emulsion or is covalently linked directly or indirectly to X, and wherein:

1) X—Y' has an oxidation potential between 0 and about 1.4 V;
2) the oxidized form of X—Y' undergoes a bond cleavage reaction to give the radical X· and the leaving fragment Y'; and
3) the radical X· has an oxidation potential ≦-0.7V (that is, equal to or more negative than about -0.7V).

It is to be understood that if Y' is H, Δ is bonded to X, i.e., the compound is of formula (a).

In this patent application, oxidation potentials are reported as "V" which represents "volts versus a saturated calomel reference electrode".

ADVANTAGEOUS EFFECT OF THE INVENTION

This invention provides a silver halide photographic emulsion containing protected fragmentable two-electron donor compounds that release an organic electron donor capable of enhancing both the intrinsic sensitivity and, if a dye is present, the spectral sensitivity of the silver halide emulsion. An important feature of these compounds is that they contain a protective group to be eliminated at development. The protected FED is effectively inert during the preparation, coating, and storage but becomes activated during processing of the photographic element. It is desirable to attach such a protective group to the FED so that the beneficial sensitizing effects can be obtained with lower amounts of unwanted fog

DETAILED DESCRIPTION OF THE INVENTION

The photographic element of this invention comprises a silver halide emulsion layer containing a compound of formula (a), (b) or (c):

 (a)

 (b)

 (c)

wherein Δ is protective group that is eliminated during development, t is a timing group, m is an integer from 0 to 3, and XY' is a fragmentable electron donor moiety in which X is an electron donor group and Y' is a leaving proton H or a leaving group Y, with the proviso that if Y' is a proton, a base, β⁻, is present in the emulsion or is covalently linked directly or indirectly to X, and XY' is a fragmentable electron donor moiety as defined below.

The protective group α is eliminated by components of a processing solution at development, such as hydroxyl ion, sulfite ion, a color developing agent, or hydroxylamine. The scission mechanism thereof includes, for example, a direct scission, such as intermolecular nucleophilic substitution reaction or elimination reaction, and an indirect breaking, such as intermolecular addition reaction or intramolecular nucleophilic substitution reaction. Examples of the protective group represented by Δ include a group cleaving on hydrolysis (e.g., acyl group, sulfonyl group, sulfinyl group, aminomethyl group), a group cleaving on reverse Michael addition reaction (e.g., 2-cyanoethyl group, 2-acylethyl group, 2-sulfonylethyl group, 2-carbamoylethyl group, pyrrolidine-2,5-3-yl group), a group cleaving on addition-release reaction (e.g., uracyl group, 2-cyclohexanone-3-yl group, maleinimido-3-yl group, 2-alkoxycaronylethenyl group, 2-acylethenyl group), a group cleaving on intramolecular electron transfer reaction (e.g., quinonemethide production cleaving group), a group cleaving on intramolecular nucleophilic substitution reaction (e.g., 3-acylpropanoyl group, 2-acyl-2,2-dialkylacetyl group), a group blocked with a phthalide group or a saccharin group and a group blocked with an imidomethyl group.

Of them, a group cleaving on reverse Michael addition reaction, a group cleaving on addition-release reaction, and a group cleaving on intramolecular nucleophilic substitution reaction are preferred.

Protecting groups that are useful for the release of photographically useful groups have been described in U.S. Pat. Nos. 4,421,845, 4,652,516, 4,698,297 5,256,525, 5,302,498, 5,019,492 and 5,830,625, the entire disclosures of which are incorporated herein by reference.

t represents a timing group and examples thereof include those described in U. S. Pat. Nos. 4,146,396, 4,248,962, 4,772,537 and 5,019,492, British Patent 1,531,927, 2,096, 783, JP-A- 57-56837, the entire disclosures of which are incorporated herein by reference. When m is greater than 1, the t groups may be the same or different.

Preferred examples of the timing group t include the following:

1. a group using a cleavage reaction of hemiacetal and examples thereof include those described in U.S. Pat. No. 4,146,396, JP-A-60-249148 and JP-A-60-249149, the entire disclosures of which are incorporated herein by reference;
2. a group causing a cleavage reaction using an intramolecular nucleophilic substitution reaction and examples thereof include those described in U.S. Pat No. 4,428, 962, the entire disclosures of which are incorporated herein by reference;
3. a group causing a cleavage reaction using an electron transfer reaction along a conjugated system and examples thereof include those described in U.S. Pat. Nos. 4,409,323 and 4,421,845, the entire disclosures of which are incorporated herein by reference;
4. a group using a cleavage reaction by hydrolysis of an ester and examples thereof include those described in West German Patent (OLS) No. 2,626,315, the entire disclosures of which are incorporated herein by reference; and
5. a group using a cleavage reaction of iminoacetal and examples thereof include those described in U.S. Pat. No. 4,546,073, the entire disclosures of which are incorporated herein by reference.

Specific examples of $\Delta$ and $(t)_m-\Delta$ are set forth below. In each example of $(t)_m-\Delta$ the part represented by t shows a timing moiety and the part represented by $\Delta$ shows a $\Delta$ moiety.

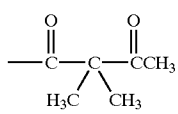

(1)

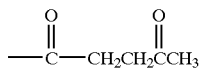

(2)

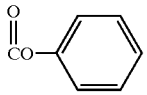

(3)

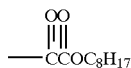

(4)

(5)

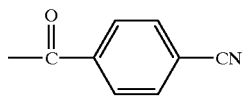

(6)

(7)

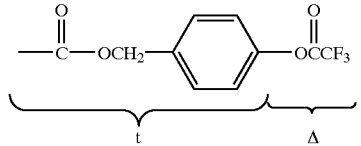

(8)

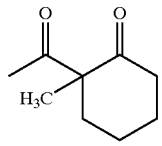

(9)

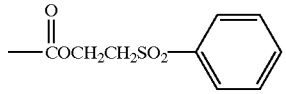

(10)

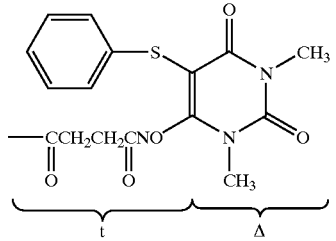

(11)

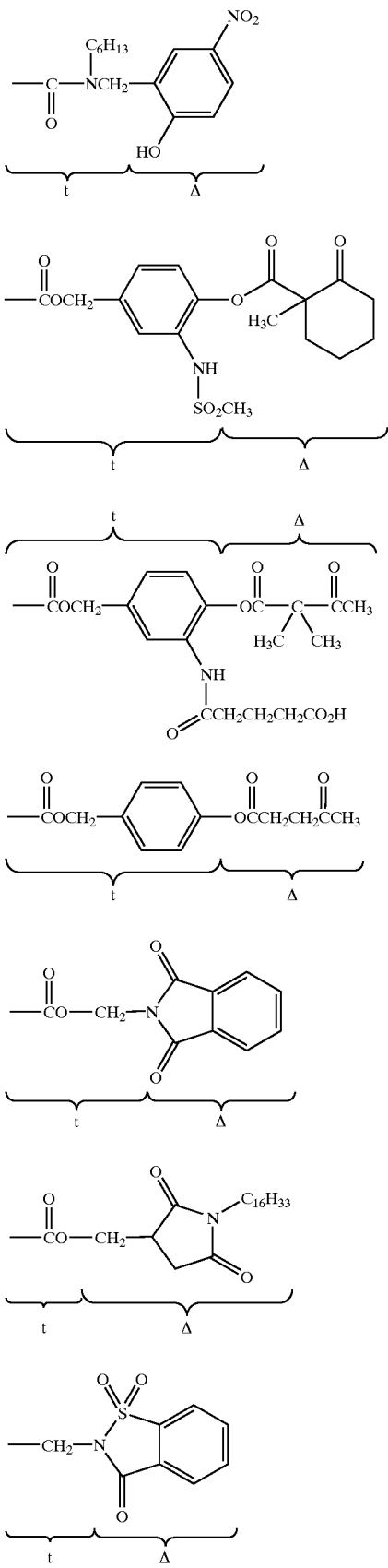
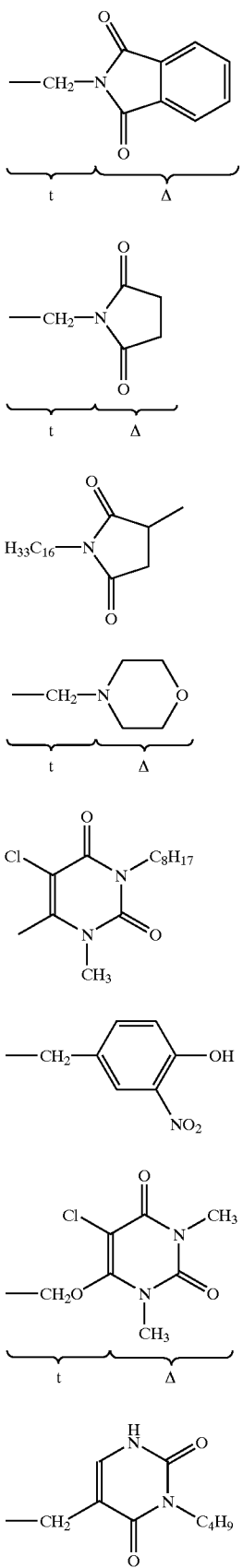

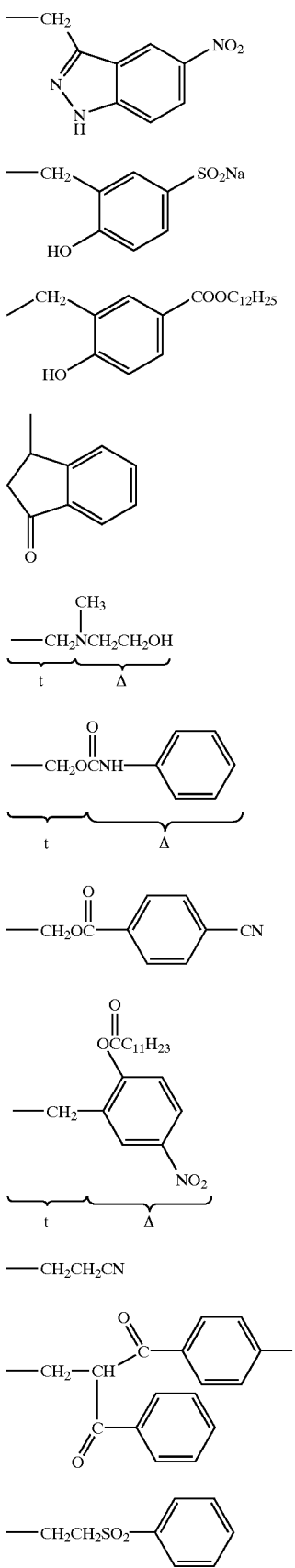

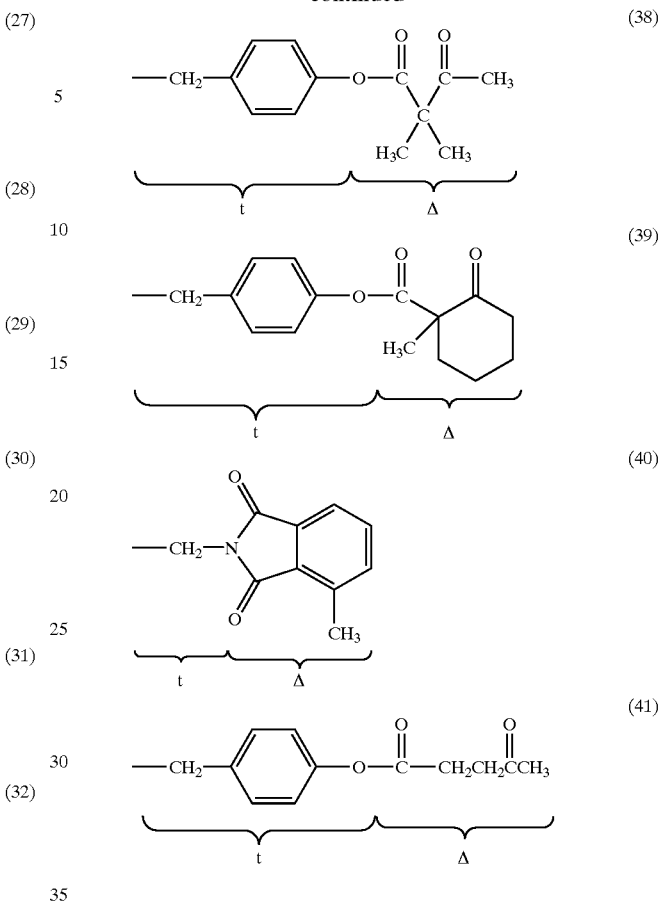

Among these specific examples (1), (2), (3), (4), (5), (6), (7), (9), (10), (21), (23), (24), (26), (27), (28), (29), (30), (33), (35), (36), (37) are examples of Δ. Others are specific examples of $-(t)_m-\Delta$. In addition to the specific examples shown above, other various combinations of Δ and $-(t)_m-$ may be used in this invention.

The moiety X—Y' in formula I, II or III represents a fragmentable electron donating (FED) compound which enhances the sensitivity of the emulsion. The inventive compounds of the formula (a), (b) or (c) are referred to herein as protected fragmentable electron donor (PFED). The fragmentable electron donating portion is of the formula X—Y' or a compound which contains a moiety of the formula -X—Y'; wherein X is an electron donor moiety, Y' is a leaving proton H or a leaving group Y:
1) X—Y' has an oxidation potential between 0 and about 1.4 V;
2) the oxidized form of X—Y' undergoes a bond cleavage reaction to give the radical X˙ and the leaving fragment Y'; and,
3) the radical X˙ has an oxidation potential $\leq -0.7V$ (that is, equal to or more negative than about −0.7V).

In embodiments of the invention wherein Y' is a proton, a base, β, is present in the emulsion being sensitized with the PFED compound or is covalently linked to X.

In embodiments of the invention in which Y' is Y, the following represents the reactions that are believed to take place when X—Y undergoes oxidation and fragmentation to produce a radical X˙, which in a preferred embodiment undergoes further oxidation.

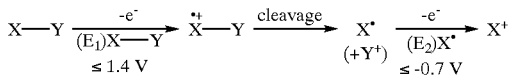

where $E_1$ is the oxidation potential of X—Y and $E_2$ is the oxidation potential of the radical X·.

$E_1$ is preferably no higher than about 1.4 V and preferably less than about 1.0 V. The oxidation potential is preferably greater than 0, more preferably greater than about 0.3 V. $E_1$ is preferably in the range of about 0 to about 1.4 V, and more preferably from about 0.3 V to about 1.0 V.

In the invention the oxidation potential, $E_2$, of the radical X· is equal to or more negative than −0.7V, preferably more negative than about −0.9 V. $E_2$ is preferably in the range of from about −0.7 to about −2 V, more preferably from about −0.8 to about −2 V and most preferably from about −0.9 to about −1.6 V.

The structural features of X—Y are defined by the characteristics of the two parts, namely the fragment X and the fragment Y. The structural features of the fragment X determine the oxidation potential of the X—Y molecule and that of the radical X·, whereas both the X and Y fragments affect the fragmentation rate of the oxidized molecule X—Y·+.

In embodiments of the invention in which Y' is H, the following represents the reactions believed to take place when the compound X—H undergoes oxidation and deprotonation to the base, β−, to produce a radical X·, which in a preferred embodiment undergoes further oxidation.

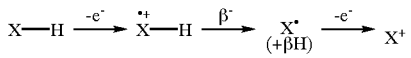

Preferred X groups are of the general formula:

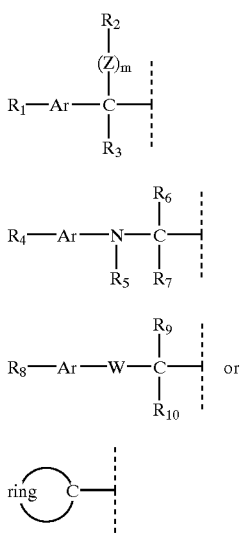

The symbol "R" (that is R without a subscript) is used in all structural formulae in this patent application to represent a hydrogen atom or an unsubstituted or substituted alkyl group.

In structure (I):
  m=0, 1;
  Z=O, S, Se, Te;
  Ar=aryl group (e.g., phenyl, naphthyl, phenanthryl, anthryl); or heterocyclic group (e.g., pyridine, indole, benzimidazole, thiazole, benzothiazole, thiadiazole, etc.);
  $R_1$=R, carboxyl, amide, sulfonamide, halogen, $NR_2$, $(OH)_n$, $(OR')_n$, or $(SR)_n$;
  R'=alkyl or substituted alkyl;
  n=1–3;
  $R_2$=R, Ar';
  $R_3$=R, Ar';
  $R_2$ and $R_3$ together can form 5- to 8-membered ring;
  $R_2$ and Ar= can be linked to form 5- to 8-membered ring;
  $R_3$ and Ar= can be linked to form 5- to 8-membered ring;
  Ar'=aryl group such as phenyl, substituted phenyl, or heterocyclic group (e.g., pyridine, benzothiazole, etc.)
  R=a hydrogen atom or an unsubstituted or substituted alkyl group.

In structure (II):
  Ar=aryl group (e.g., phenyl, naphthyl, phenanthryl); or heterocyclic group (e.g., pyridine, benzothiazole, etc.);
  $R_4$=a substituent having a Hammett sigma value of −1 to +1, preferably −0.7 to +0.7, e.g., R, OR, SR, halogen, CHO, C(O)R, COOR, $CONR_2$, $SO_3R$, $SO_2NR_2$, $SO_2R$, SOR, C(S)R, etc;
  $R_5$=R, Ar'
  $R_6$ and $R_7$=R, Ar'
  $R_5$ and Ar= can be linked to form 5- to 8-membered ring;
  $R_6$ and Ar= can be linked to form 5- to 8-membered ring (in which case, $R_6$ can be a hetero atom);
  $R_5$ and $R_6$ can be linked to form 5- to 8-membered ring;
  $R_6$ and $R_7$ can be linked to form 5- to 8-membered ring;
  Ar'=aryl group such as phenyl, substituted phenyl, heterocyclic group;
  R=hydrogen atom or an unsubstituted or substituted alkyl group.

A discussion on Hammett sigma values can be found in C. Hansch and R. W. Taft *Chem. Rev.* Vol 91, (1991) p 165, the disclosure of which is incorporated herein by reference.

In structure (III):
  W=O, S, Se;
  Ar=aryl group (e.g., phenyl, naphthyl, phenanthryl, anthryl); or heterocyclic group (e.g., indole, benzimidazole, etc.)
  $R_8$=R, carboxyl, $NR_2$, $(OR)_n$, or $(SR)_n$ (n=1–3);
  $R_9$ and $R_{10}$=R, Ar';
  $R_9$ and Ar= can be linked to form 5- to 8-membered ring;
  Ar'=aryl group such as phenyl substituted phenyl or heterocyclic group;
  R=a hydrogen atom or an unsubstituted or substituted alkyl group.

In structure (IV):
  "ring" represents a substituted or unsubstituted 5-, 6- or 7-membered unsaturated ring, preferably a heterocyclic ring.

The following are illustrative examples of the group X of the general structure I:

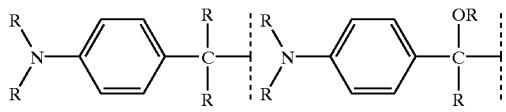

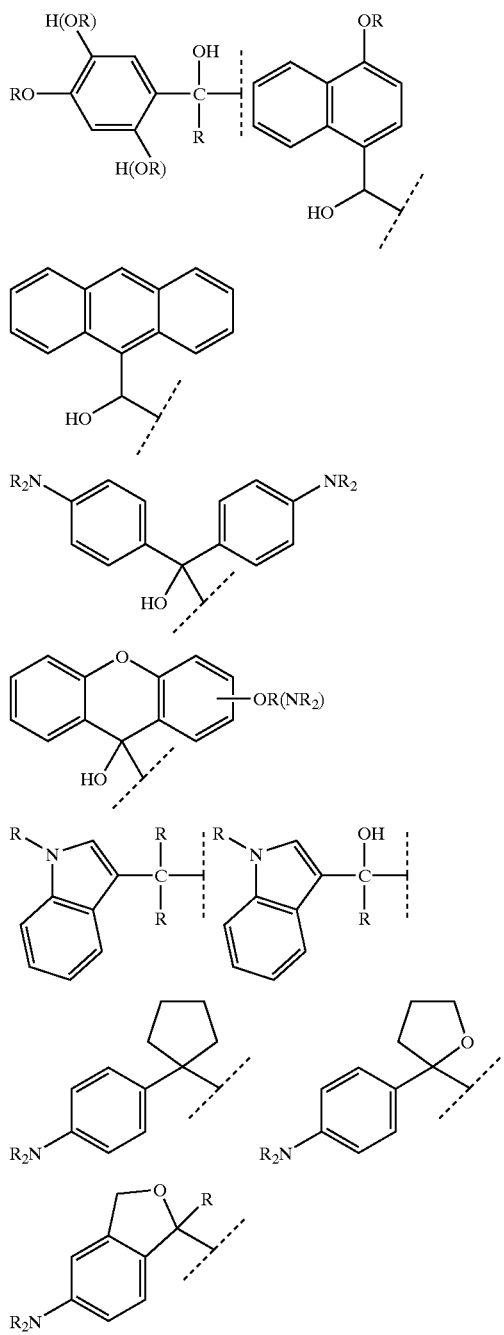

In the structures of this patent application a designation such as —OR(NR$_2$) indicates that either —OR or —NR$_2$ can be present.

The following are illustrative examples of the group X of general structure

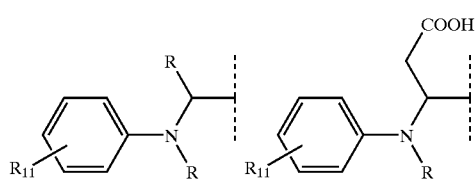

$Z_1$=a covalent bond, S, O, Se, NR, CR$_2$, CR=CR, or CH$_2$CH$_2$.

$Z_2$=S, O, Se, NR, CR$_2$, CR=CR, R$_{13}$, =alky, substituted alkyl or aryl, and R$_{14}$=H, alkyl substituted alkyl or aryl.

The following are illustrative examples of the group X of the general structure III:

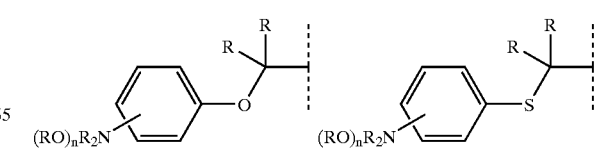

-continued

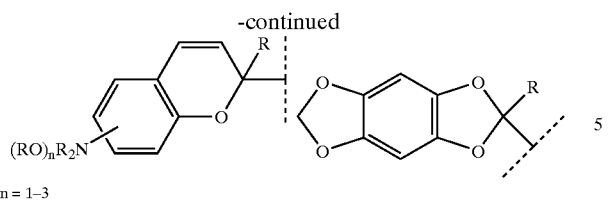

n = 1–3

The following are illustrative examples of the group X of the general structure IV:

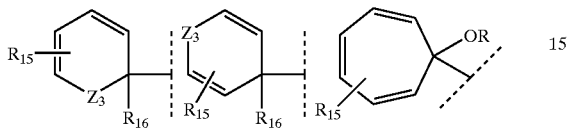

$Z_3$=O, S, Se, NR $R_{15}$=R, OR, $NR_2$ $R_{16}$=alkyl, substituted alkyl

Preferred Y' groups are:

(1) X', where X' is an X group as defined in structures I–IV and may be the same as or different from the X group to which it is attached

 (2)

 (3)

where M = Si, Sn or Ge; and R' = alkyl or substituted alkyl

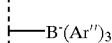 (4)

where Ar″ = aryl or substituted aryl

 (5)

In preferred embodiments of this invention Y' is —H, —COO⁻ or —Si(R')$_3$ or —X'. Particularly preferred Y' groups are —H, —COO⁻ or —Si(R')$_3$.

In embodiments of the invention in which Y' is a proton, a base, β⁻, is present in the emulsion or, preferably, is covalently linked directly or indirectly to X. The base is preferably the conjugate base of an acid of pKa between about 1 and about 8, preferably about 2 to about 7. Collections of pKa values are available (see, for example: Dissociation Constants of Organic Bases in Aqueous Solution, D. D. Perrin (Butterworths, London, 1965); CRC Handbook of Chemistry and Physics, 77th ed, D. R. Lide (CRC Press, Boca Raton, Fla., 1996)). Examples of useful bases are included in Table I.

TABLE I pKa's in water of the conjugate acids of some useful bases

| Base | pKa |
|---|---|
| $CH_3$—$CO_2^-$ | 4.76 |
| $C_2H_5$—$CO_2^-$ | 4.87 |
| $(CH_3)_2CH$—$CO_2^-$ | 4.84 |
| $(CH_3)_3C$—$CO_2^-$ | 5.03 |
| HO—$CH_2$—$CO_2^-$ | 3.83 |
| 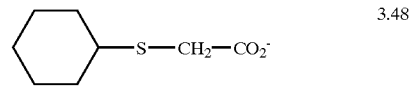 | 3.48 |
| $CH_3$—CO—NH—$CH_2$—$CO_2^-$ | 3.67 |
| 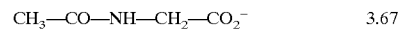 | 4.19 |
| 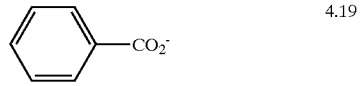 | 4.96 |
| $CH_3$—$COS^-$ | 3.33 |
| 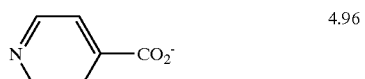 | 3.73 |
|  | 4.88 |
| 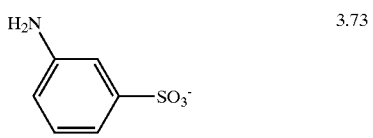 | 4.01 |
| 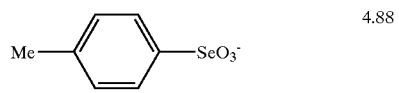 | 4.7 |
| $(CH_3)_3N^+$—$O^-$ | 4.65 |
| $H_2N$—$CH_2$—$\overset{+}{CH}$—$NH_3$ $\underset{CH_3}{|}$ | 6.61 |
|  | 5.25 |
| 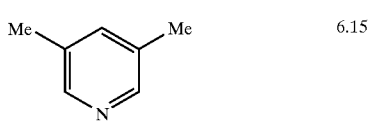 | 6.15 |

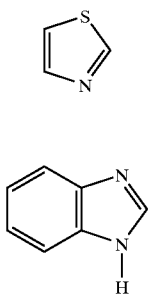 2.44

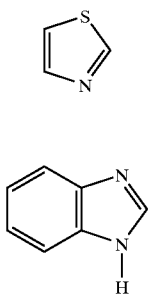 5.53

Preferably the base, β⁻ is a carboxylate, sulfate or amine oxide.

In some embodiments of the invention, the fragmentable electron donating compound contains a light absorbing group, Z, which is attached directly or indirectly to X, a silver halide absorptive group, A, directly or indirectly attached to X, or a chromophore forming group, Q, which is attached to X. Such fragmentable electron donating compounds are preferably of the following formulae:

Z—(L—X—Y')$_k$

A—(L—X—Y')$_k$ (A—L)$_k$—X—Y'

Q—X—Y'

A—(X—Y')$_k$ (A)$_k$—X—Y'

Z—(X—Y')$_k$ or (Z)$_k$—X—Y'

Z is a light absorbing group;

k is 1 or 2;

A is a silver halide adsorptive group that preferably contains at least one atom of N, S, P, Se, or Te that promotes adsorption to silver halide;

L represents a linking group containing at least one C, N, S, P or O atom; and

Q represents the atoms necessary to form a chromophore comprising an amidinium-ion, a carboxyl-ion or dipolar-amidic chromophoric system when conjugated with X—Y'.

Z is a light absorbing group including, for example, cyanine dyes, complex cyanine dyes, merocyanine dyes, complex merocyanine dyes, homopolar cyanine dyes, styryl dyes, oxonol dyes, hemioxonol dyes, and hemicyanine dyes.

Preferred Z groups are derived from the following dyes:

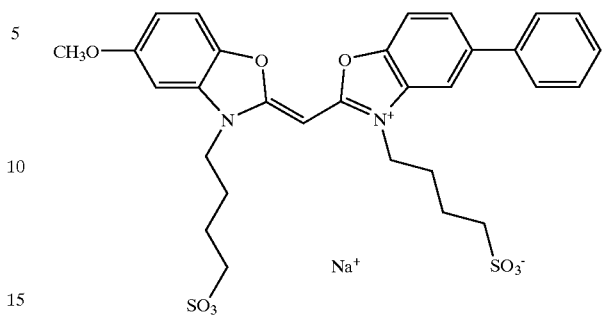

Dye 1

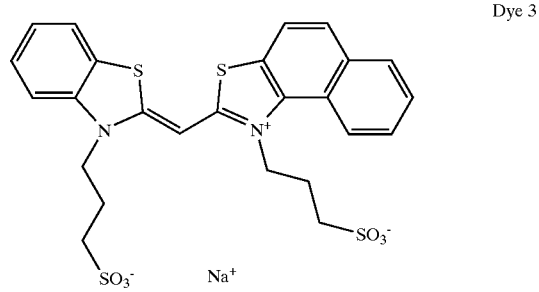

Dye 3

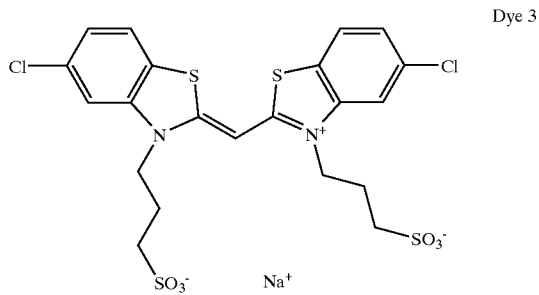

Dye 3

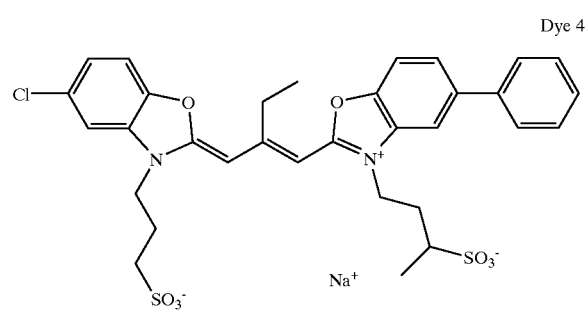

Dye 4

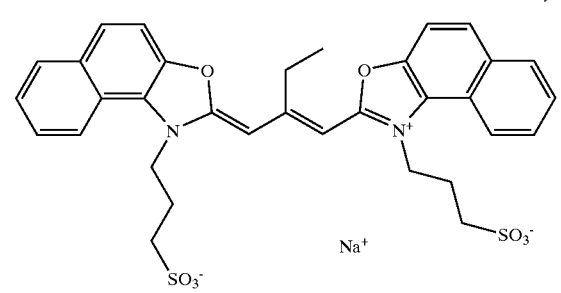

Dye 5

-continued

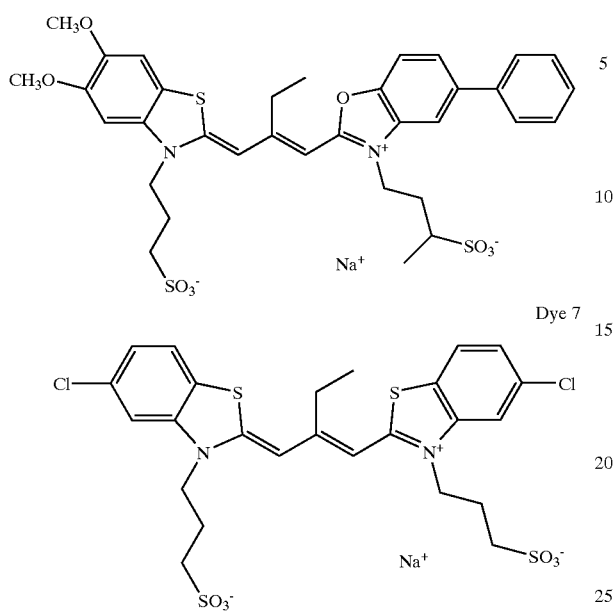

Dye 6

Dye 7 and

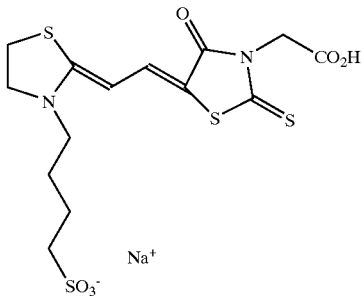

Dye 8

The linking group L may be attached to the dye at one (or more) of the heteroatoms, at one (or more) of the aromatic or heterocyclic rings, or at one (or more) of the atoms of the polymethine chain, at one (or more) of the heteroatoms, at one (or more) of the aromatic or heterocyclic rings, or at one (or more) of the atoms of the polymethine chain. For simplicity, and because of the multiple possible attachment sites, the attachment of the L group is not specifically indicated in the generic structures.

The silver halide adsorptive group A is preferably a silver-ion ligand moiety or a cationic surfactant moiety. In preferred embodiments, A is selected from the group consisting of. i) sulfur acids and their Se and Te analogs, ii) nitrogen acids, iii) thioethers and their Se and Te analogs, iv) phosphines, v) thionamides, selenamides, and telluramides, and vi) carbon acids.

Illustrative A groups include:

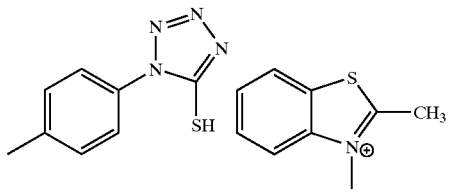

-continued

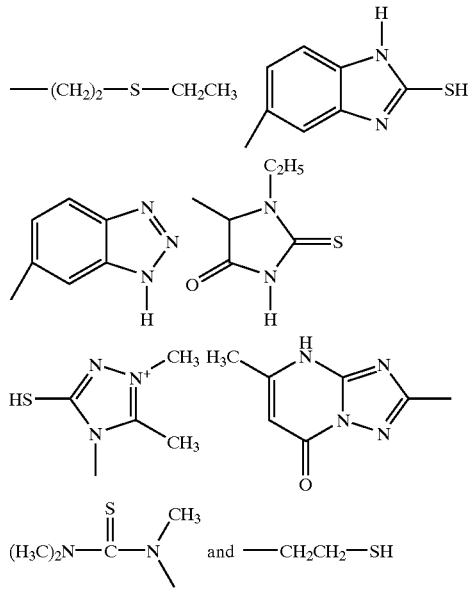

The point of attachment of the linking group L to the silver halide adsorptive group A will vary depending on the structure of the adsorptive group, and may be at one (or more) of the heteroatoms, at one (or more) of the aromatic or heterocyclic rings.

The linkage group represented by L which connects by a covalent bond the light absorbing group Z or the silver halide adsorptive group A to the fragmentable electron donating group XY is preferably an organic linking group containing a least one C, N, S, or O atom. It is also desired that the linking group not be completely aromatic or unsaturated, so that a pi-conjugation system cannot exist between the Z (or A) and XY moieties. Preferred examples of the linkage group include, an alkylene group, an arylene group, —O—, —S—, —C=O, —SO$_2$—, —NH—, —P=O, and —N=. Each of these linking components can be optionally substituted and can be used alone or in combination. Examples of preferred combinations of these groups are:

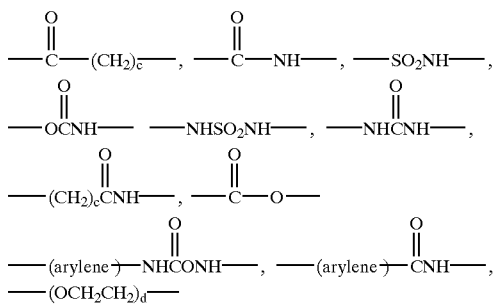

where c=1–30, and d=1–10

The length of the linkage group can be limited to a single atom or can be much longer, for instance up to 30 atoms in length. A preferred length is from about 2 to 20 atoms, and most preferred is 3 to 10 atoms. Some preferred examples of L can be represented by the general formulae indicated below:

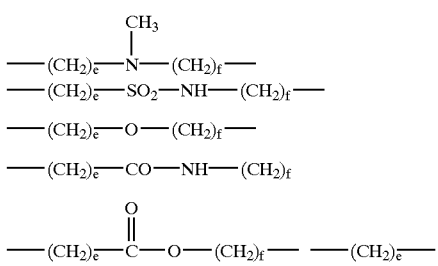

e and f=1–30, with the proviso that e+f≦31

Q represents the atoms necessary to form a chromophore comprising an amidinium-ion, a carboxyl-ion or dipolar-amidic chromophoric system when conjugated with X—Y'. Preferably the chromophoric system is of the type generally found in cyanine, complex cyanine, hemicyanine, merocyanine, and complex merocyanine dyes as described in F. M. Hamer, *The Cyanine Dyes and Related Compounds* (Interscience Publishers, New York, 1964).

Illustrative Q groups include:

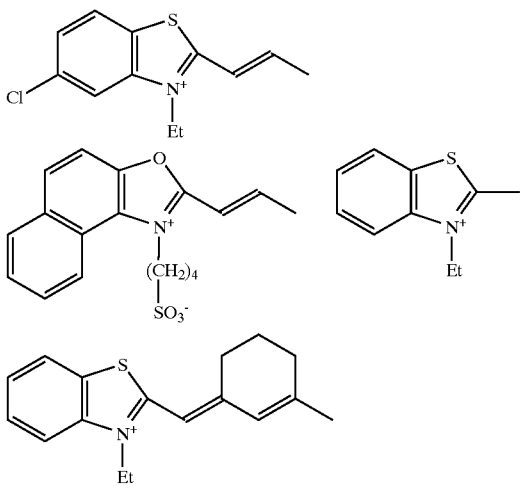

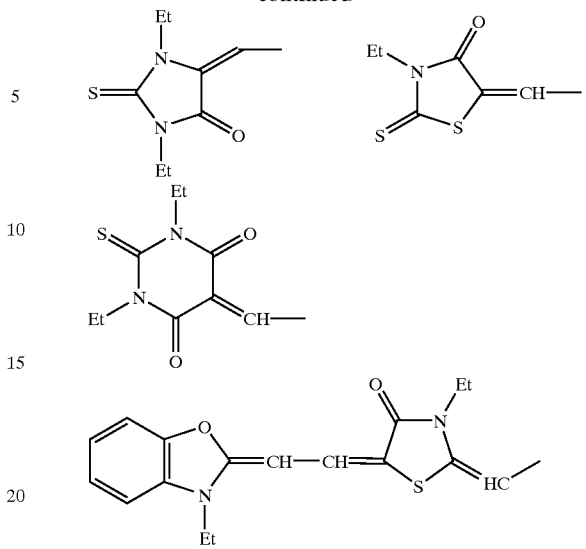

Particularly preferred are Q groups of the formula:

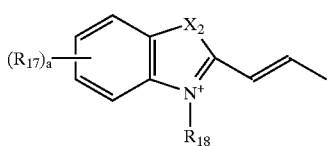

wherein:

$X_2$ is O, S, N, or $C(R_{19})_2$, where $R_{19}$ is substituted or unsubstituted alkyl each $R_{17}$ is independently a hydrogen atom, a halogen atom, a substituted or unsubstituted alkyl group, or substituted or unsubstituted aryl group;

a is an integer of 1–4; and $R_{18}$ is substituted or unsubstituted alkyl, or substituted or unsubstituted aryl.

Illustrative fragmentable two-electron donating (FED) moieties XY' include:

FED 1

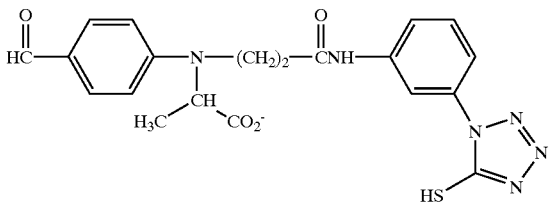

FED 2

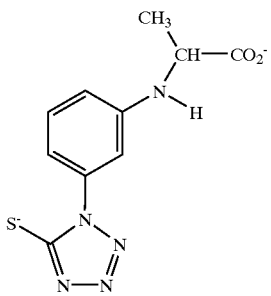

FED 3
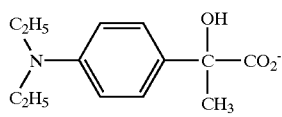
FED 4
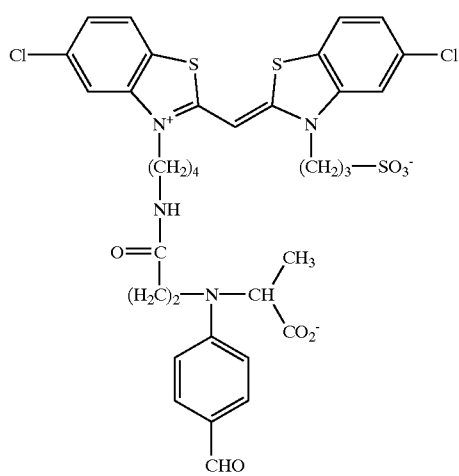
FED 5
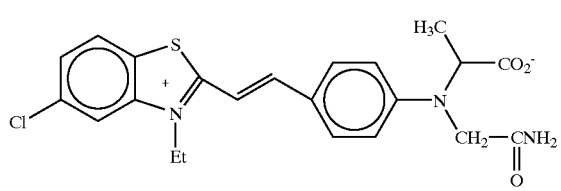
FED 6
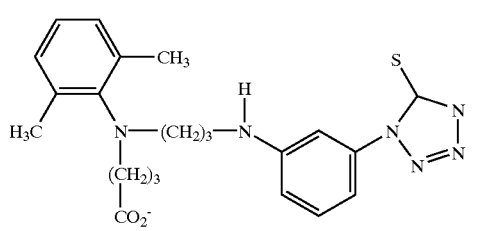
FED 7
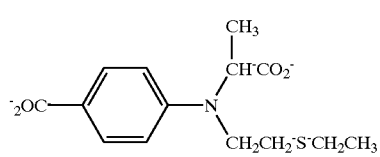
FED 8
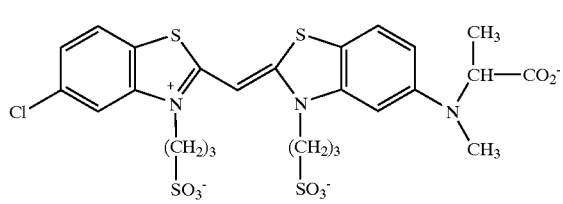
FED 9
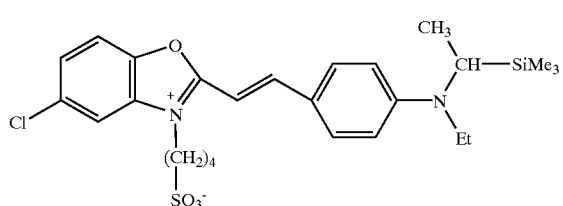

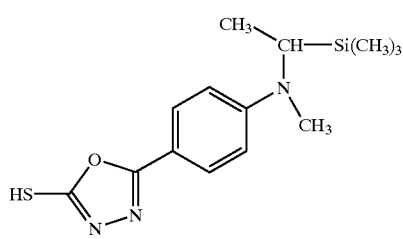
FED 11
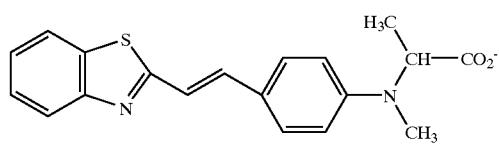
FED 12
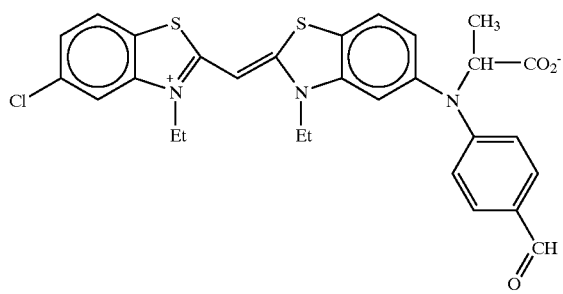
FED 13
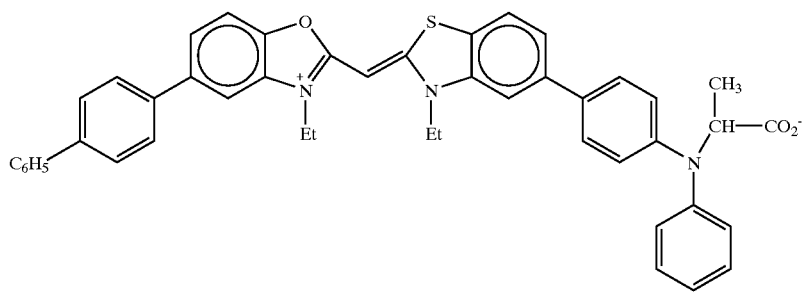
FED 14
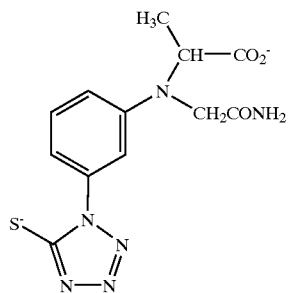
FED 15

-continued
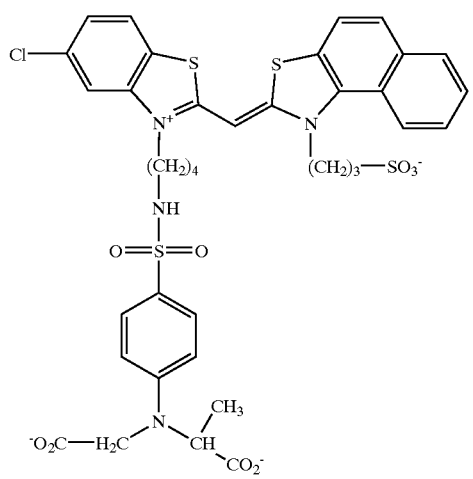
FED 16
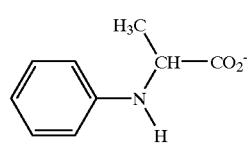
FED 18
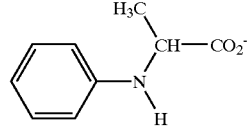
FED 19
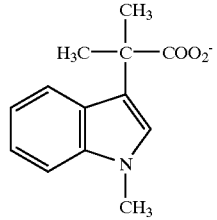
FED 20
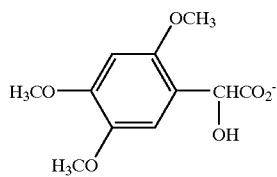
FED 21
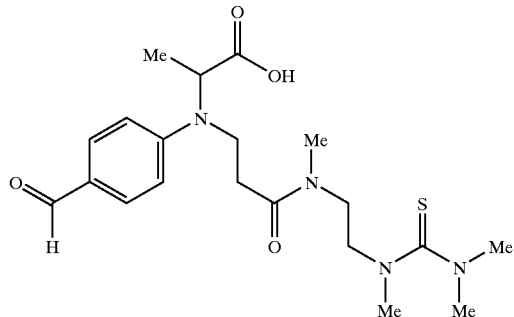
FED 22
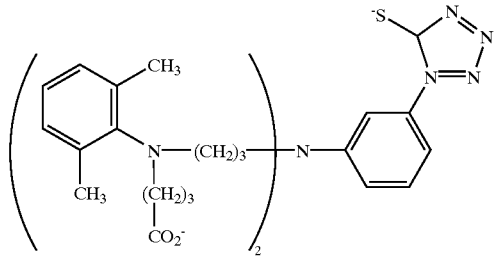

Fragmentable electron donating compounds XY' are described more fully in U.S. Pat. Nos. 5,747,235, 5,747,236, 5,994,051, 6,010,841, 6,054,260 and 6,153,371, the entire disclosures of these patents are incorporated herein by reference.

The position of attachment of the protecting group $(t)_m-\Delta$ or $\Delta$ (when m=0) to the moiety XY' will vary depending on the structures of $(t)_m-\Delta$, $\Delta$, and of XY'. The group $(t)_m-\Delta$ or $\Delta$ (when m=0) can be attached to the X and portion of the XY' moiety to give $\Delta-(t)_m-XY'$) or they may be attached to the Y' and portion of the XY' moiety to give $XY'-(t)_m-\Delta$). (As noted above, when Y' is a proton, $(t)_m-\Delta$ or $\Delta$ (when m=0) cannot be attached to Y' and is attached to X). When attached to the X portion of XY' the purpose of $\Delta$ and $(t)_m-\Delta$ is to render the XY' moiety inactive, by raising the one-electron oxidation potential $E_1$ of XY' to a value more positive than the 1.4 V threshold. When attached to the Y portion of XY' the purpose of $\Delta$ and $(t)_m-\Delta$ is to render the XY' moiety inactive by preventing the fragmentation reaction of XY'$^{-\bullet}$. Only when $(t)_m-\Delta$ is eliminated (during the development) does the XY' portion of the molecule become active and capable of increasing the sensitivity of silver halide.

For attachment to the X portion of XY' the group $(t)_m-\Delta$ or $\Delta$ (when m=0) must contain an terminal acyl group for binding to X. Examples of $\Delta$ and $(t)_m-\Delta$ that are suitable for connection to X include (1) through (17). For the X group in structures (I), (II), and (IV), the protecting group $(t)_m-\Delta$ or $\Delta$ (when m=0) should be attached directly to the nitrogen atom (of the aniline, indole, or N-containing ring) to form a carbamate derivative. The direct attachment of $(t)_m-\Delta$ or $\Delta$ (when m=0) to the nitrogen atom substantially raises (makes more positive) the oxidation potential $E_1$ of the XY' group, thereby stabilizing the XY' moiety and suppressing the initial one-electron oxidation (of X—Y to X—Y$^{\bullet+}$) that is necessary for the XY' to provide the sensitivity increase to silver halide.

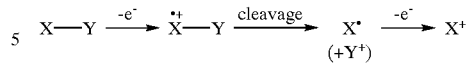

On the other hand, for XY' that do not contain a nitrogen atom (for example, as an aniline, indole, or N-heterocyclic functionality), or where the X group is of the type (III), the attachment of $(t)_m-\Delta$ or $\Delta$ (when m=0) to X will not necessarily raise the $E_1$ and in this circumstance a protecting group must be attached to the Y' portion of the XY' moiety to give $XY'-(t)_m-\Delta$.

The protecting group $(t)_m-\Delta$ or $\Delta$ (when m=0) may be attached to the Y' portion of the XY' moiety in the cases where the leaving group Y' is COO$^-$. The attachment of $(t)_m-\Delta$ or $\Delta$ (when m=0) to the COO$^-$ moiety yields an ester derivative of XY' and thereby prevents the moiety XY'$^{+\bullet}$ from undergoing the cleavage (fragmentation) reaction and precludes the formation of the neutral radical species X$^\bullet$. In embodiments of the invention in which Y' is a proton and the base, $\beta$, is covalently linked to X, the protecting group $(t)_m-\Delta$ or $\Delta$ (when m=0) may be attached to the base $\beta^-$ to give an ester derivative thereby inactivating the attached base $\beta^-$ until the protecting group is removed (in the developer). For attachment to the Y' portion of XY' the group $(t)_m-\Delta$ or $\Delta$ (when m=0) must contain an terminal methylene group for binding to the COO$^-$ moiety. Examples of $\Delta$ and $(t)_m-\Delta$ that are suitable for connection to Y' include (17) through (41).

In some molecules $(t)_m-\Delta$ or $\Delta$ may be attached to both the X and Y' portions or XY' moiety (providing Y' is not a proton), respectively, to give $\Delta-(t)_m-XY'-(t)_m-\Delta$.

Specific structures for the protected fragmentable electron donors (PFED) of the formulas (a), (b) or (c) include the following:

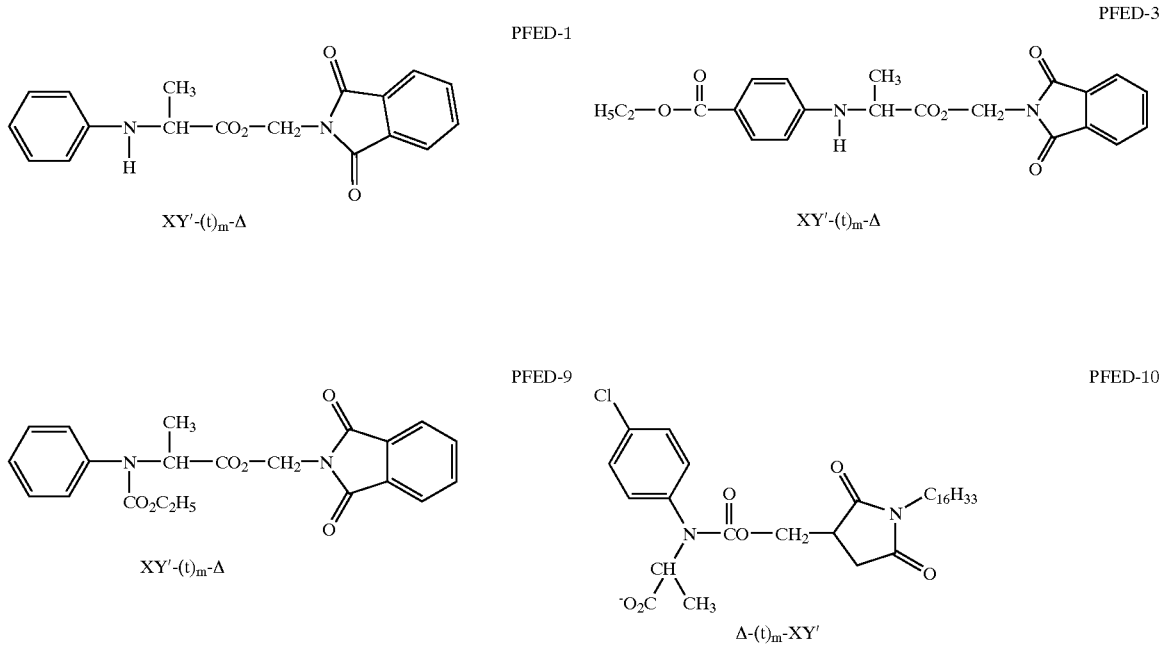

-continued
PFED-12
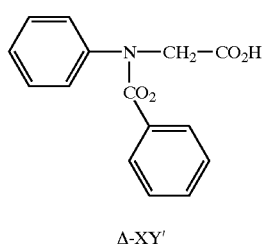
Δ-XY'
PFED-13
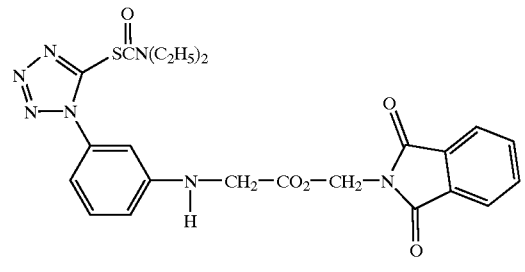
XY'-(t)$_m$-Δ
PFED-14
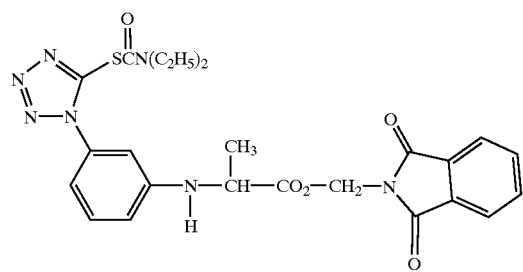
XY'-(t)$_m$-Δ
PFED-15
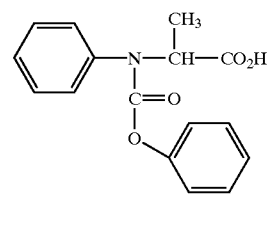
Δ-XY'
PFED-16
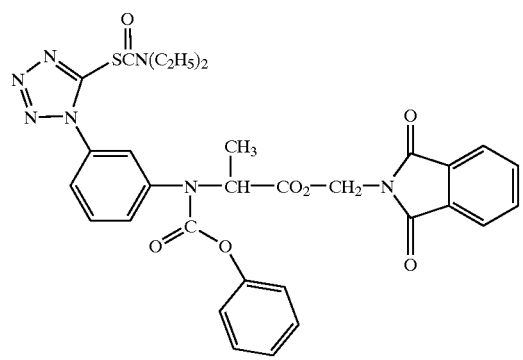
XY'-(t)$_m$-Δ
PFED-17
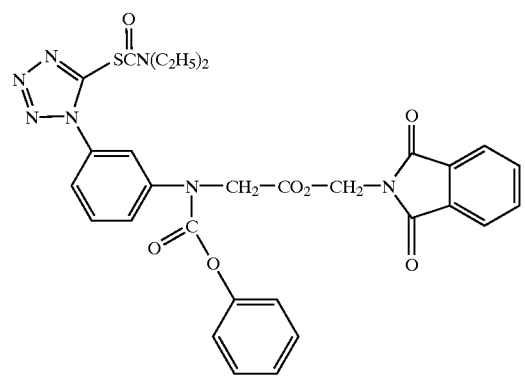
Δ-XY'-(t)$_m$-Δ
PFED-18
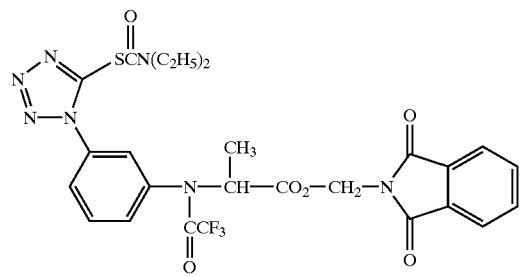
Δ-XY'-(t)$_m$-Δ
PFED-19
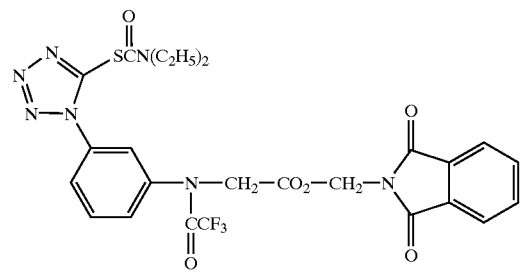
Δ-XY'-(t)$_m$-Δ

-continued
PFED-20
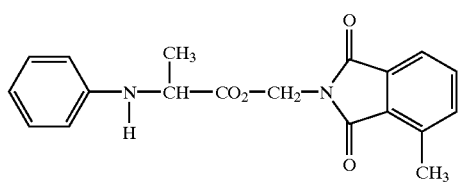
XY'-(t)ₘ-Δ
PFED-21
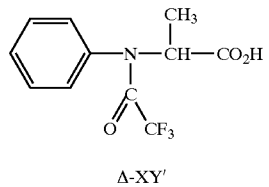
Δ-XY'
PFED-22
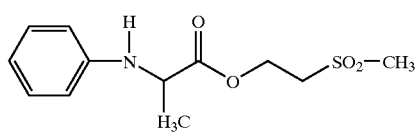
XY'-(t)ₘ-Δ
PFED-23
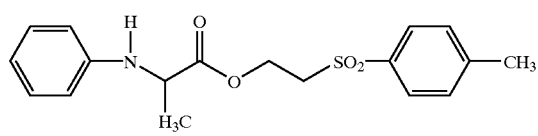
XY'-(t)ₘ-Δ
PFED-24
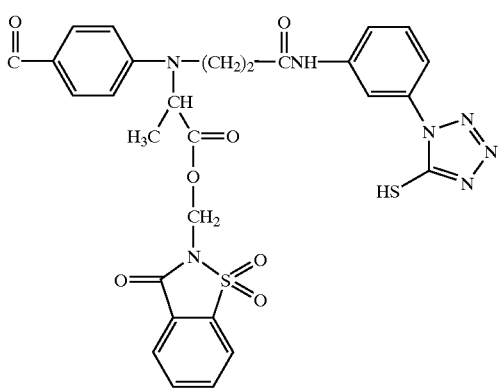
XY'-(t)ₘ-Δ
PFED-25
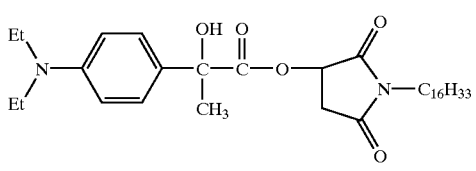
XY'-Δ
PFED-26
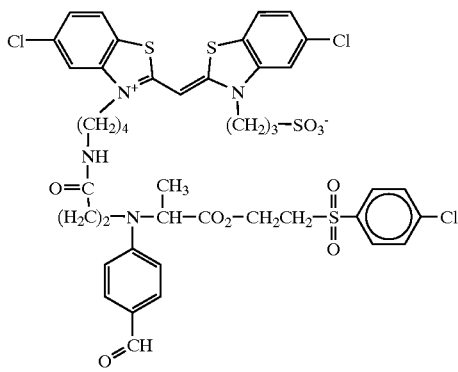
XY'-(t)ₘ-Δ
PFED-27
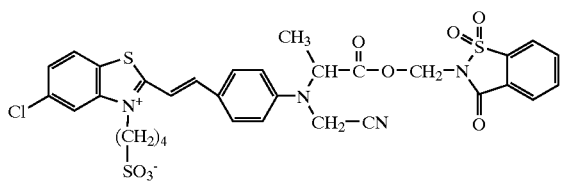
XY'-(t)ₘ-Δ

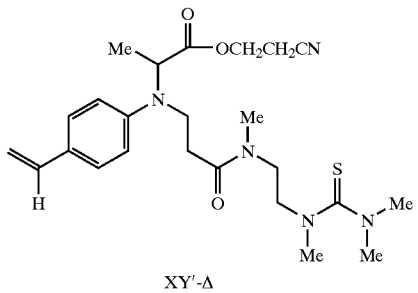

PFED-28

XY'-Δ

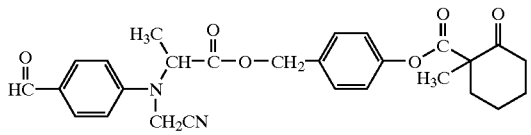

PFED-29

XY'-(t)ₘ-Δ

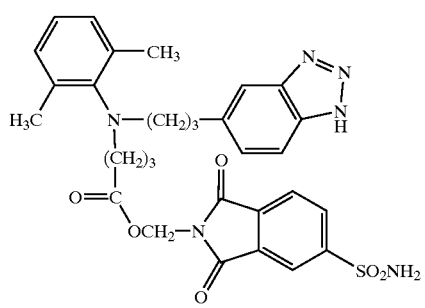

PFED-30 attached to base β⁻

XY'-(t)ₘ-Δ

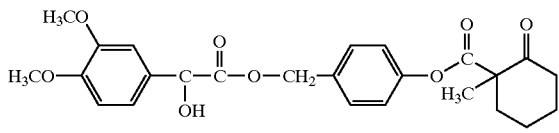

PFED-31

XY'-(t)ₘ-Δ

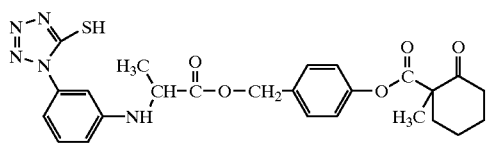

PFED-32

XY'-(t)ₘ-Δ

Table II compares oxidation potential data for the moiety XY' with several compounds of the formula Δ-XY'. These data show that the attachment of Δ to the nitrogen atom (that is, the acylation of the nitrogen) to give the corresponding carbamate derivative significantly raises $E_1$ of XY'. The measured $E_1$ for the Δ-XY' are found to be greater than 1.5 V. Thus, compounds of the structure Δ-XY' wherein the moiety is attached to the nitrogen atom of XY' are "protected" because $E_1$ criteria (1), as outlined above and which states "X—Y' has an oxidation potential between 0 and about 1.4 V", is no longer satisfied. When the protecting group is removed, for example by a component of the developer solution, the oxidation potential $E_1$ for XY' lies within the potential limits of 0 to 1.4V.

Table II

| Compound | Type of PFED | $E_1$ (V vs SCE) |
|---|---|---|
| 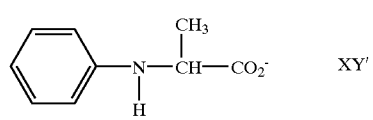 | XY' | 0.52 |
| 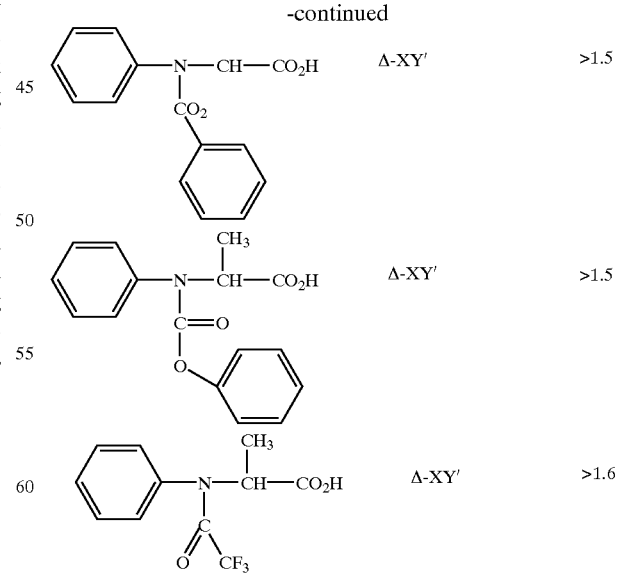 | Δ-XY' | >1.5 |
| | Δ-XY' | >1.5 |
| | Δ-XY' | >1.6 |

The protected fragmentable electron donors of the present invention can be included in a silver halide emulsion by direct dispersion in the emulsion, or they may be dissolved in a solvent such as water, methanol or ethanol for example, or in a mixture of such solvents, and the resulting solution can be added to the emulsion. The compounds of the present invention may also be added from solutions containing a base and/or surfactants, or may be incorporated into aqueous slurries or gelatin dispersions and then added to the emulsion. The protected fragmentable electron donor may be used as the sole sensitizer in the emulsion. However, in preferred embodiments of the invention a sensitizing dye is also added to the emulsion. The compounds can be added before, during or after the addition of the sensitizing dye. The amount of electron donor which is employed in this invention may range from as little as $1\times10^{-8}$ mole per mole of silver in the emulsion to as much as about 0.1 mole per mole of silver, preferably from about $5\times10^{-7}$ to about 0.05 mole per mole of silver. Where the oxidation potential $E_1$ for the XY moiety of the electron donating sensitizer is a relatively low potential, it is more active, and relatively less agent need be employed. Conversely, where the oxidation potential for the XY moiety of the electron donating sensitizer is relatively high, a larger amount thereof, per mole of silver, is employed. In addition, for XY moieties that have silver halide adsorptive groups A or light absorptive groups Z or chromophoric groups Q directly or indirectly attached to X, the fragmentable electron donating sensitizer is more closely associated with the silver halide grain and relatively less agent need be employed.

Various compounds may be added to the photographic material of the present invention for the purpose of lowering the fogging of the material during manufacture, storage, or processing. Typical antifoggants are discussed in Section VI of Research Disclosure I, for example tetraazaindenes, mercaptotetrazoles, polyhydroxybenzenes, hydroxyaminobenzenes, combinations of a thiosulfonate and a sulfinate, and the like.

For this invention, polyhydroxybenzene and hydroxyaminobenzene compounds (hereinafter "hydroxybenzene compounds") are preferred as they are effective for lowering fog without decreasing the emulsion sensitivity. Examples of hydroxybenzene compounds are:

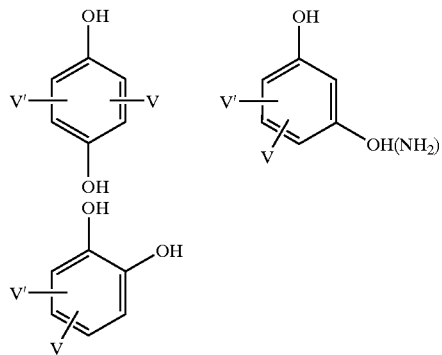

In these formulae, V and V' each independently represent —H, —OH, a halogen atom, —OM (M is alkali metal ion), an alkyl group, a phenyl group, an amino group, a carbonyl group, a sulfone group, a sulfonated phenyl group, a sulfonated alkyl group, a sulfonated amino group, a carboxyphenyl group, a carboxyalkyl group, a carboxyamino group, a hydroxyphenyl group, a hydroxyalkyl group, an alkylether group, an alkylphenyl group, an alkylthioether group, or a phenylthioether group.

More preferably, they each independently represent —H, —OH, —Cl, —Br, —COOH, —CH$_2$CH$_2$COOH, —CH$_3$, —CH$_2$CH$_3$, —C(CH$_3$)3, —OCH$_3$, —CHO, —SO$_3$K, —SO$_3$Na, —SO$_3$H, —SCH$_3$, or -phenyl.

Especially preferred hydroxybenzene compounds follow:

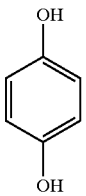

HB1

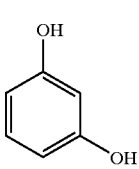

HB2

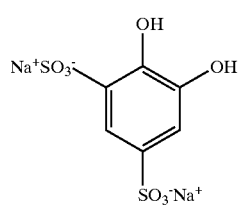

HB3

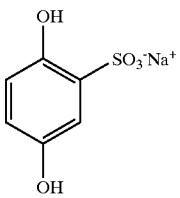

HB4

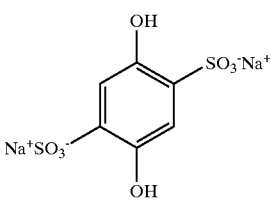

HB5

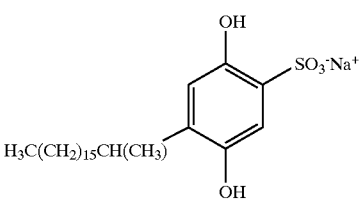

HB6

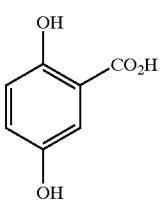

HB7

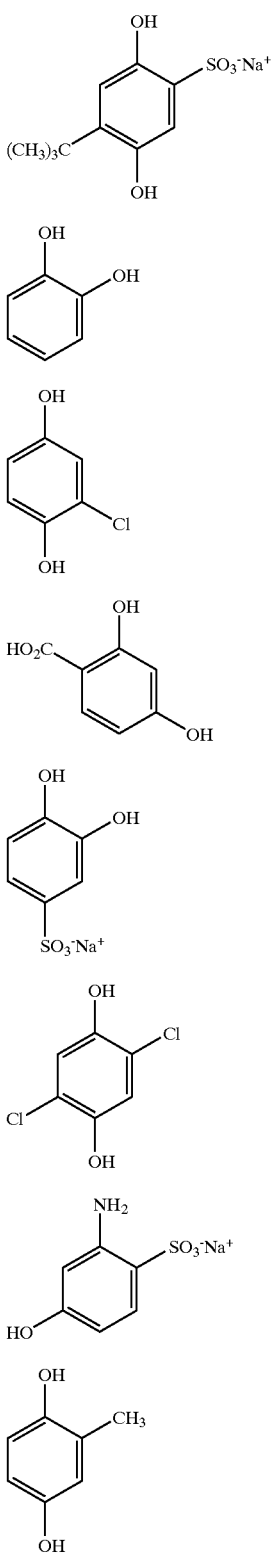

Hydroxybenzene compounds may be added to the emulsion layers or any other layers constituting the photographic material of the present invention. The preferred amount added is from $1\times10^{-3}$ to $1\times10^{-1}$ mol, and more preferred is $1\times10^{-3}$ to $2\times10^{-2}$ mol, per mol of silver halide.

Photographic elements of the present invention may also usefully include a magnetic recording material as described in Research Disclosure, Item 34390, November 1992, or a transparent magnetic recording layer such as a layer containing magnetic particles on the underside of a transparent support as in U.S. Pat. No. 4,279,945 and U.S. Pat. No. 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support).

The present invention also contemplates the use of photographic elements of the present invention in what are often referred to as single use cameras (or "film with lens" units). Single use cameras are well known and typically comprise (1) a plastic inner camera shell including a taking lens, a film metering mechanism, and a simple shutter and (2) a paper-cardboard outer sealed pack which contains the inner camera shell and has respective openings for the taking lens and for a shutter release button, a frame counter window, and a film advance thumbwheel on the camera shell. The camera may also have a flash unit to provide light when the picture is taken. The inner camera shell has front and rear viewfinder windows located at opposite ends of a see-through viewfinder tunnel, and the outer sealed pack has front and rear openings for the respective viewfinder windows. At the manufacturer, the inner camera shell is loaded with a film cartridge, and substantially the entire length of the unexposed filmstrip is factory prewound from the cartridge into a supply chamber of the camera shell. After the customer takes a picture, the thumbwheel is manually rotated to rewind the exposed frame into the cartridge. The rewinding movement of the filmstrip the equivalent of one frame rotates a metering sprocket to decrement a frame counter to its next lower numbered setting. When substantially the entire length of the filmstrip is exposed and rewound into the cartridge, the single-use camera is sent to a photofinisher who first removes the inner camera shell from the outer sealed pack and then removes the filmstrip from the camera shell. The filmstrip is processed, and the camera shell and the opened pack are thrown away.

In the following discussion of suitable materials for use in elements of this invention, reference will be made to Research Disclosure, September 1996, Number 389, Item 38957, which will be identified hereafter by the term "Research Disclosure I." The Sections hereafter referred to are Sections of the Research Disclosure I unless otherwise indicated. The foregoing references and all other references cited in this application are incorporated herein by reference.

The silver halide emulsions employed in the photographic elements of the present invention may be negative-working, such as surface-sensitive emulsions or unfogged internal latent image forming emulsions, or positive working emulsions of the internal latent image forming type (that are fogged during processing). Suitable emulsions and their preparation as well as methods of chemical and spectral sensitization are described in Sections I through V. Color materials and development modifiers are described in Sections V through XX. In particular image dye-forming couplers are described in Section X, paragraph B. Vehicles which can be used in the photographic elements are described in Section II, and various additives such as brighteners, antifoggants, stabilizers, light absorbing and scattering materials, hardeners, coating aids, plasticizers, lubricants and matting agents are described, for example, in Sections VI through XIII. Manufacturing methods are described in all of the sections, layer arrangements particularly in Section XI, exposure alternatives in Section XVI, and processing methods and agents in Sections XIX and XX.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213 490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. No. 4,163,669; U.S. Pat. No. 4,865,956; and U.S. Pat. No. 4,923,784 are particularly useful. Also contemplated is the use of nucleating agents, development accelerators or their precursors (UK Patent 2,097,140; U.K. Patent 2,131,188); development inhibitors and their precursors (U.S. Pat. No. 5,460,932; U.S. Pat. No. 5,478,711); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019, 492.

The photographic elements may further contain other image-modifying compounds such as "Development Inhibitor-Releasing" compounds (DIR's). Useful additional DIR's for elements of the present invention, are known in the art and examples are described in U.S. Pat. Nos. 3,137, 578; 3,148,022; 3,148,062; 3,227,554; 3,384,657; 3,379, 529; 3,615,506; 3,617,291; 3,620,746; 3,701,783; 3,733, 201; 4,049,455; 4,095,984; 4,126,459; 4,149,886; 4,150, 228; 4,211,562; 4,248,962; 4,259,437; 4,362,878; 4,409, 323; 4,477,563; 4,782,012; 4,962,018; 4,500,634; 4,579, 816; 4,607,004; 4,618,571; 4,678,739; 4,746,600; 4,746, 601; 4,791,049; 4,857,447; 4,865,959; 4,880,342; 4,886, 736; 4,937,179; 4,946,767; 4,948,716; 4,952,485; 4,956, 269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), deionized gelatin, gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions.

Photographic elements of the present invention are preferably imagewise exposed using any of the known techniques, including those described in *Research Disclosure I*, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements comprising the composition of the invention can be processed in any of a number of well-known photographic processes utilizing any of a number of well-known processing compositions, described, for example, in *Research Disclosure I*, or in T. H. James, editor, *The Theory of the Photographic Process*, 4th Edition, Macmillan, N.Y., 1977. In the case of processing a negative working element, the element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog silver halide (usually chemical fogging or light fogging), followed by treatment with a color developer. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N -(β-(methanesulfonamido) ethylaniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

Dye images can be formed or amplified by processes which employ in combination with a dye-image-generating reducing agent an inert transition metal-ion complex oxidizing agent, as illustrated by Bissonette U.S. Pat. Nos. 3,748,138, 3,826,652, 3,862,842 and 3,989,526 and Travis U.S. Pat. No. 3,765,891, and/or a peroxide oxidizing agent as illustrated by Matejec U.S. Pat. No. 3,674,490, *Research*

Disclosure, Vol. 116, December, 1973, Item 11660, and Bissonette Research Disclosure, Vol. 148, August, 1976, Items 14836, 14846 and 14847. The photographic elements can be particularly adapted to form dye images by such processes as illustrated by Dunn et al U.S. Pat. No. 3,822,129, Bissonette U.S. Pat. Nos. 3,834,907 and 3,902,905, Bissonette et al U.S. Pat. No. 3,847,619, Mowrey U.S. Pat. No. 3,904,413, Hirai et al U.S. Pat. No. 4,880,725, Iwano U.S. Pat. No. 4,954,425, Marsden et al U.S. Pat. No. 4,983,504, Evans et al U.S. Pat. No. 5,246,822, Twist U.S. Pat. No. 5,324,624, Fyson EPO 0 487 616, Tannahill et al WO 90/13059, Marsden et al WO 90/13061, Grimsey et al WO 91/16666, Fyson WO 91/17479, Marsden et al WO 92/01972. Tannahill WO 92/05471, Henson WO 92/07299, Twist WO 93/01524 and WO 93/11460 and Wingender et al German OLS 4,211,460.

Development is followed by bleach-fixing, to remove silver or silver halide, washing and drying.

Synthesis Examples

Typical examples of synthesis of compounds follow. Other compounds can also be synthesized by analogy using appropriate selected known staring materials.

Preparation of Glycine, N-(phenyl), Ethyl Ester

To a stirred suspension of 21.4 g of aniline and 82.5 g of anhydrous potassium carbonate in 300 mL of acetonitrile under a nitrogen atmosphere was added 50 g of ethyl-2-bromoproprionate, and 4.6 g of potassium iodide. The reaction mixture was refluxed under nitrogen for 2 days, the solution was cooled, and the salt was filtered out. The filtrate was poured into dichloromethane and washed with aqueous sodium bicarbonate solution, then washed with water. Anhydrous sodium sulfate was added and then the dichloromethane solution was filtered. The filtrate was concentrated by evaporation, and then distilled under vacuum to give 20.8 g of the desired product (a colorless oil)

Preparation of N-phenylalanine t-Butyl Ester

A mixture of aniline (9.30 g, 0.10 mol), 2-bromopropionate t-butyl ester 20.9 g, 0.10 mol), Hunig's base (12.90 g, 0.10 mol) and toluene (200 mL) were stirred at reflux for 16 hours. The salt that formed was removed by filtration and the filtrate concentrated in vacuo to an oil (20 g). The oil was distilled. Pure N-phenylalanine t-butyl ester (18.0 g, 81% yield) was collected at 105–115 C (0.08 mm Hg).

$^1$H NMR (300 MHz, CDCl$_3$): 1.45 (bm, 12H), 4.05 (bm 2H), 6.60 (bd, 2H), 6.70 (bt, 1H), 7.12 (bt, 2H). APT NMR (75 MHz, CDCl$_3$): 18.81, 27.93, 52.56, 81.20, 113.42, 117.00, 129.16, 146.50, 172.80.

Preparation of PFED 1

A mixture of N-phenylalanine sodium salt (0.936 g, 5 mmol), N-bromomethylphthalimide (1.200 g, 5 mmol) and DMF (6 mL) were stirred at 25 C for 64 hours. Diethyl ether was added to precipitate the sodium bromide that formed in the reaction. The filtrate was concentrated in vacuo at 60 C. The resulting oil was partitioned between ethyl acetate and water. The ethyl acetate extract was dried with magnesium sulfate and concentrated in vacuo to give crude PFED-1. Diethyl ether was added and the resulting solid PFED-1 was collected (0.6 g, 38% yield).

ESMS$^+$ 325. $^1$H NMR (300 MHz, CDCl$_3$): 1.48 (d, 3H), 4.15 (m, 2H), 5.70 (d, 1H), 5.82 (d, 1H), 6.55 (d, 2H), 6.65 (t, 1H), 7.08 (t, 2H), 7.25 (m, 2H), 7.40 (m, 2H). APT NMR (75 MHz, DMSO/CDCl$_3$): 16.21, 49.54, 58.85, 110.89, 115.20, 122.01, 127.09, 129.50, 133.27, 145.20, 164.00, 171.90.

Preparation of PFED 20

A mixture of N-phenylalanine sodium salt (1.87 g, 10 mmol), N-chloromethylphthalimide (2.09 g, 10 mmol) and DMF (10 mL) were stirred at 25 C for 16 hours. Diethyl ether (50 mL) was added to precipitate the sodium chloride that was formed in the reaction. The salt was removed by filtration, and the filtrate concentrated in vacuo at 95 C to an oil (3.8 g). The oil was purified by flash chromatography (silica gel, 1 ethyl acetate: 1 ligroin) to give pure PFED-20 as a solid (2.8 g, 83% yield).

ESMS$^+$ 339. $^1$H NMR (300 MHz, CDCl$_3$): 1.50 (d, 3H), 2.70 (s, 3H), 4.18 (m, 2H), 5.68 (d, 2H), 5.80 (d, 2H), 6.55 (d, 2H), 6.60 (t, 1H), 7.08 (t, 2H), 7.50 (d, 1H), 7.60 (t, 3H), 7.70 (d, 2H) APT NMR (75 MHz, CDCl$_3$): 14.13, 17.62, 51.94, 61.0, 113.39, 118.33, 121.47, 128.20, 129.14, 131.90, 134.02, 136.83, 138.40, 146.00, 166.20, 166.80, 173.00.

Preparation of Internediate I

Trifluoroacetic anhydride (2.10 g, 10 mmol) was added over 1 minute to a solution of N-phenylalanine t-butyl ester (2.21 g, 10 mmol), lutidine (1.07 g, 10 mmol) and diethyl ether (10 mL). The mixture was stirred at 25 C for 16 hours. The mixture was washed with water (3×10 mL) and the water discarded. The ether layer was dried with magnesium sulfate and concentrated in vacuo to a yellow oil (2.86 g). Flash chromatography (silica gel, 1 ethyl acetate: 1 ligroin) afforded the trifluoroacetamide (2.66 g, 84%).

$^1$ H NMR (300 MHz, CDCl$_3$): 1.30 (d, 3H), 1.50 (s, 9H), 4.65 (q, 4H), 7.40 (bs, 5H). APT NMR (75 MHz, CDCl$_3$): 14.62, 27.89, 59.03, 81.05, 111.00, 114.60, 118.20, 121.80, 129.17, 129.37, 129.46, 137.00, 156.30, 156.60, 156.90, 157.20, 169.00.

Preparation of Intermediate II

A mixture of N-phenylalanine t-butyl ester (15.2 g, 0.07 mol), Hunig's base (9.0 g, 0.07 mol) and toluene was chilled to 20 C. To this solution was added phosgene in toluene (1.93 M solution, 36 mL, 0.07 mol) over 0.5 h, while maintaining a reaction temperature of 15–20 C. The mixture was stirred for 3 h at 15 C. The salt that formed was removed by filtration, and the filtrate was concentrated in vacuo at 35 C. Ligroin was added to the concentrate. A small quantity of solid was precipitated. The precipitate was removed by filtration, and the filtrate concentrated as before to give an oil (20 g). The composition of the oil was determined by $^1$H NMR to be ca. 88% of the desired carbamyl chloride and the remaining 12% to be the starting N-phenylalanine t-butyl ester. This material was suitable for use without further purification.

$^1$H NMR (300 MHz, CDCl$_3$): 1.32 (d, 3H), 1.52 (s, 9H), 4.60 (q, 1H), 7.35–7.45 (m, 5H).

Preparation of PFED-21

A solution of Intermediate I (2.54 g, 8 mmol) and trifluoroacetic acid (5.00 g, 44 mmol) were stirred at 25 C for 16 hours. The mixture was concentrated in vacuo at 38 C to yield an oil (2.75 g). Flash chromatography (silica gel, 1 ethyl acetate: 1 ligroin) gave a fraction rich in PFED-21. The fraction was concentrated as before. The concentrate was dissolved in diethyl ether, washed with water and the diethyl ether layer dried with magnesium sulfate. The diethyl ether was removed in vacuo to give pure PFED-21.

ESMS⁻ 260. ¹H NMR (300 MHz, CDCl₃): 1.40 (d, 3H), 4.82 (q, 1H), 7.40 (bs, 5H), 11.00 (bs, 1H). ¹H NMR (75 MHz, CDCl₃): 14.50, 57.93, 110.32, 114.13, 117.94, 121.75, 129.24, 129.51, 129.70, 136.70, 156.53, 157.00, 157.47, 157.94, 176.19.

Preparation of PFED-22

A mixture of the carbamoyl chloride Intermediate II (2.8 g, 88% pure, ca. 10 mmol), 2-(methylsulfonyl) ethanol (1.24 g, 10 mmol), Hunig's Base (1.3 g, 10 mmol) and THF (20 mL) were stirred at reflux for 16 hours. The mixture was filtered and the filtrate concentrated in vacuo at 95 C to give an oil (3.7 g). Flash chromatography (silica gel, 1 ethyl acetate: 1 ligroin) afforded the pure ester.

ESMS⁺ 272. ¹H NMR (300 MHz, CDCl₃): 1.50 (d, 3H), 2.80 (s, 3H), 3.25 (m, 21), 4.20 (q, 1H), 4.55 (m, 2H), 6.60 (d, 2H), 6.75 (tm 3H), 7.15 (m, 2H). APT NMR (75 MHz, CDCl₃): 18.69, 41.78, 52.04, 53.80, 58.20, 113.20, 118.61, 129.39, 146.00, 173.00.

Preparation of PEBD-23

A mixture of the carbamoyl chloride Intermediate II (2.8 g, 88% pure, ca. 10 mmol), 2-[(4-methylphenyl) sulfonyl] ethanol (2.0 g, 10 mmol), Hunig's Base (1.3 g, 10 mmol) and THF (20 mL) were stirred at reflux for 16 hours. The mixture was filtered and the filtrate concentrated in vacuo at 95 C to give an oil (4.6 g). Flash chromatography (silica gel, 1 ethyl acetate: 1 ligroin) afforded the pure ester (0.9 g, 26% yield.)

ESMS⁺ 348. ¹H NMR (300 MHz, CDCl₃): 1.35 (d, 3H), 2.40 (s, 3H), 3.38 (m, 2H), 3.95 (q, bs, 2H), 4.42 (m, 2H), 6.55 (d, 2H), 6.75 (t, 1H), 7.15 (m, 2H), 7.35 (d, 2H), 7.75 (d, 2H). APT NMR (75 MHz, CDCl₃): 18.47, 21.51, 51.71, 55.00, 58.00, 113.27, 118.37, 128.04, 129.57, 129.93, 136.00, 145.00, 146.00, 173.00.

Preparation of Comparison Compound, FED 18

A mixture of 11.4 g of alanine, N-phenyl, ethyl ester, 3.3 g of sodium hydroxide, 60 mL of H₂O, 60 mL of ethanol, and 80 mmL of tetrahydrofuran was refluxed for 15 hours, cooled, and the precipitated salt was collected. The solid was recrystallized from ethanol to give 7.5 g of the desired product.

The following compounds were synthesized via reaction schemes I and II:

Scheme I

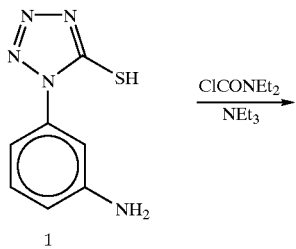

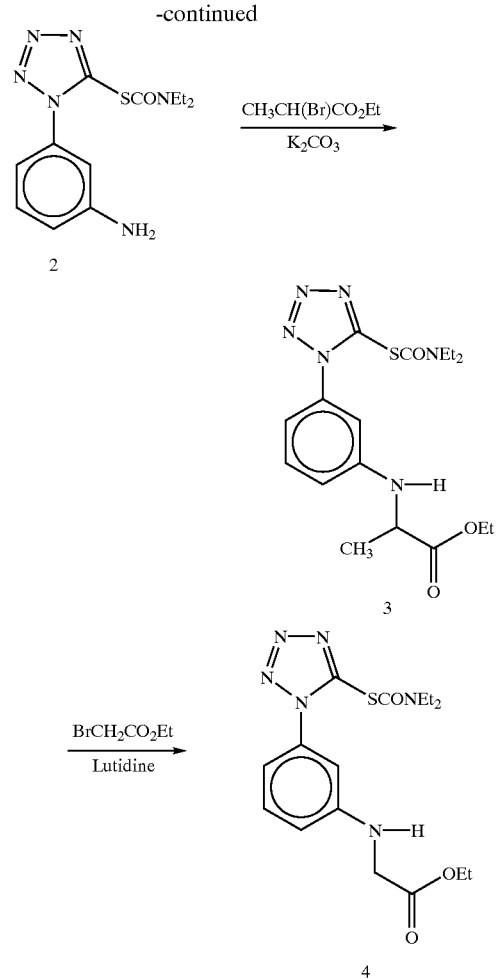

Preparation of PMT-Thiocabamate Intermediate (2)

The amino-phenylmercaptotetrazole (1) (50.0 g, 0.258 mol) was stirred with triethylamine (38.2 mL, 0.274 mol) in 450 mL of dry acetonitrile at rt. After initial dissolution a white precipitate formed. Diethylcarbamyl chloride (35 mL, 0.274 mol) was dissolved in 50 mL acetonitrile and added dropwise. The solution was then heated at reflux for 3 h. The solution was chilled in an ice bath and the precipitated triethylammonium chloride removed by filtration. The solution was concentrated at reduced pressure to yield an orange oil. This oil was filtered through a 250 g plug of silica gel using 2 L of methylene chloride. The filtrate was concentrated at reduced pressure and 50 mL of methanol was added. The methanol solution was cooled to 0° C. and a white solid formed. The solid was collected, washed with ether, and dried to yield 40.3 g of the desired intermediate product (2).

¹H NMR (DMSO-d⁶): 7.16 (t, 1H, J=7.96 Hz); 6.6–6.8 (m, 3H); 5.6 (s, 2H); 3.25 (m, 4H); 1.0 (dt, 6H, J=45 Hz, 6.7 Hz).

Preparation of Intermediate 3

A mixture of 5.84 g (0.02 mol) of 2, 3.5 g (0.025 mol) of powdered potassium carbonate, and 10 mL of ethyl 2-bromoproprionate was stirred and heated at 100° C. for 18 h under a nitrogen atm. The reaction was cooled to room temperature and ethyl acetate/water was added. The mixture was transferred to a separatory funnel. The ethyl acetate layer was separated, washed with brine and dried over anhyd. sodium sulfate. The ethyl acetate solution was filtered and concentrated at reduced pressure to yield an oil. This oil was stirred overnight with 75 mL of isopropyl ether, and a solid was produced. The solid was collected, washed with isopropyl ether, slurried in ether, recollected and air-dried. This afforded 5.7 g (73%) of a white solid, m.p. 91–93° C.

Preparation of Intermediate 4

Thiocarbamylphenylmercaptotetrazole (Intermediate 2) (1.9 g, 6.5 mmol), ethyl bromoacetate (1.1 g, 6.5 mmol) and lutidine (0.7 g, 6.5 mmol) were dissolved in 20 mL of acetonitrile and heated at 75° C. under a nitrogen atmosphere for 18 hours. The solution was than cooled and partitioned between 100 mL of ethyl acetate and 100 mL of brine. The organic layer was separated, dried over anhydrous sodium sulfate and concentrated at reduced pressure. The resulting oil was subjected to chromatography on silica gel using THF:heptane (3:2) as eluant. In this manner 1.4 g (69%) of the desired adduct (4) was obtained. $^1$H NMR (CDCl$_3$): 7.3 (m, 1H); 6.9 (m, 1H); 6.75 (m, 2H); 4.55 (m, 11); 4.2 (q, 2H); 3.9 (d, 2H); 3.3 (q, 4H); 1.3 (t, 3H); 1.2 (t, 3H); 1.1 (t, 3H). MS m/e 378

Preparation of Half Hydrolyzed Adduct 5

The ester 3 (0.5 g, 1.27 mmol) was dissolved in 20 mL of ethanol and 1 equivalent of 1N NaOH (1.27 mL) was added via syringe to the solution. It was stirred at rt overnight, then concentrated at reduced pressure. The solid was precipitated with ether to give 0.29 g (60%) of the desired product (5).

$^1$H NMR (D$_2$O): 7.4 (t, 1H); 6.9 (m, 2H); 6.78 (d, 1H); 3.8 (q, 1H); 3.4 (q, 2H); 3.25 (q, 2H); 1.4 (d, 3H); 1.2 (m, 2H); 0.95 (m, 2H).

Preparation of Half Hydrolyzed Adduct 6

The procedure described for compound 5 was used to prepare adduct 6, except ester 4 was employed as the starting material.

$^1$H NMR (D$_2$O): 7.2 (m, 1H); 6.7–6.6 (m 3H); 3.55 (s, 2H); 3.2 (q, 2H); 3.1(q, 2H); 1.0 (t, 3H); 0.8 (t, 3H). ESMS m/e 349

Scheme II

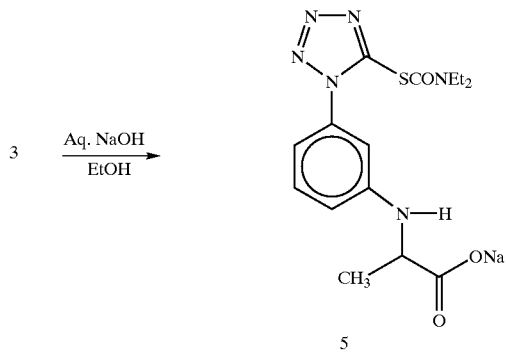

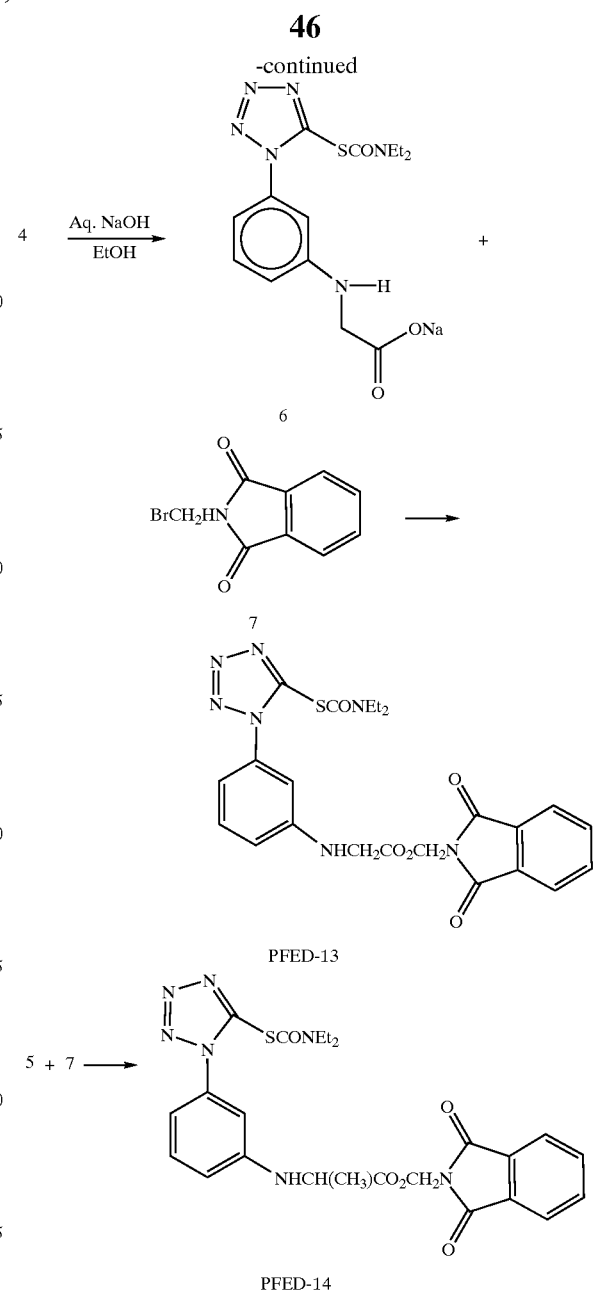

The half hydrolyzed adduct (6) (1.1 g, 2.96 mmol) was dissolved in 5 mL of DMF and the phthalamido-bromide (7) (0.7 g, 2.9 mmol) was added. The mixture was stirred 24 hours at room temperature and then partitioned between 200 mL of ethyl acetate and 150 mL of brine. The organic layer was separated, and washed two times with 100 mL of brine. The organic phase was then dried over anhyd. sodium sulfate and concentrated at reduced pressure. The resulting material was subjected to chromatography on silica gel using heptane:THF 1:1 as eluant and 1.0 g of the desired PFED-13 was isolated.

$^1$H NMR (CDCl$_3$): 7.95 (br s, 2H); 7.8 (br s, 2H); 7.3 (m, 1H); 6.9(d, 1H); 6.75(br s, 2H); 5.85 (s, 2H); 4.0 (s, 2H); 3.35(m, 4H); 1.3 (m, 3H); 1.05(m, 3H). ESMS m/e 510

Preparation of PFED-14

The half hydrolyzed adduct (5) (2.4 g, 6.2 mmol) was dissolved in 10 mL of DMF and the phthalamido-bromide (7) (1.4 g, 5.8 mmol) was added. The mixture was stirred 24 hours at room temperature and then partitioned between 200 mL of ethyl acetate and 150 mL of brine. The organic layer was separated, and washed two times with 100 mL of brine. The organic phase was then dried over anhydrous sodium sulfate and concentrated at reduced pressure. The resulting material was subjected to chromatography on silica gel using heptane:THF 1:4 as the eluant and 1.5 g of the desired PFED-14 was isolated.

$^1$H NMR (CDCl$_3$): 7.75 (m, 2H); 7.6 (m, 2H); 7.1 (m, 1H); 6.7(m, 1H); 6.6 (br s, 2H); 5.6 (s, 2H); 4.0 (m, 1H); 3.2 (m, 4H); 1.3 (d, 3H); 1.1 (m 3H); 0.9 (m, 3H). FDMS m/e 523

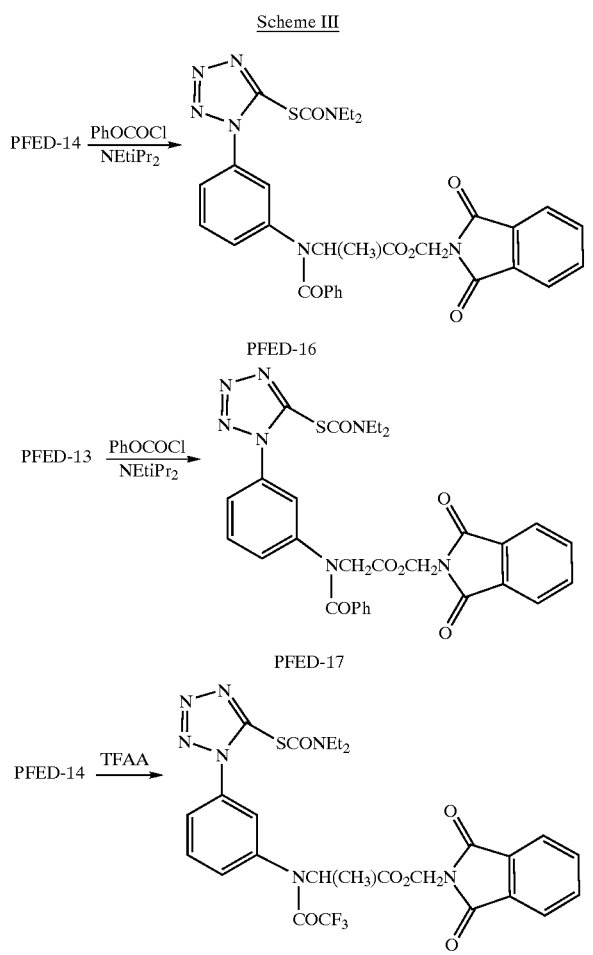

Preparation of PFED-16

The phthalamido-blocked compound PFED-14 (0.8 g, 1.5 mmol), phenylchloroformate (0.24 g, 1.5 mmol) and diisopropylethylamine (0.2 g, 1.5 mmol) were dissolved in 5 mL of THF and the mixture was heated at 50° C. for 24 hours. The reaction mixture was then partitioned between ethyl acetate (100 mL) and brine (100 mL). The organic layer was separated, dried over anhydrous sodium sulfate and concentrated at reduced pressure. The resulting material was chromatographed on silica gel using THF:heptane 1:1 as eluant, which yielded the desired PFED-16.

$^1$H NMR(CDCl$_3$): 7.95–7.6 (m, 9H); 7.35–7.05 (m, 4H); 5.85 (s, 2H); 4.9 (q, 1H); 3.2 (m, 4H); 1.5 (d, 3H); 1.15 (m, 3H); 1.0 (m, 3H). FDMS m/e 643

Preparation of PFED-17

The phthalamido-blocked compound PFED-13 (0.8 g, 1.57 mmol), phenylchloroformate (0.25 g, 1.6 mmol) and diisopropylethylamine (0.21 g, 1.6 mmol) were dissolved in 10 mL of THF and the mixture was heated at 50° C. for 24 hours. The reaction mixture was then partitioned between ethyl acetate (100 mL) and brine (100 mL). The organic layer was separated, dried over anhydrous sodium sulfate and concentrated at reduced pressure. The resulting material was chromatographed on silica gel using THF:heptane 1:1 as eluant, which yielded the desired PFED-17.

$^1$H NMR(CDCl$_3$): 8.0–7.4 (m, 8H); 7.4–7.1 (m, 5H); 5.9 (s, 2H); 4.5 (m, 2H); 3.2 (m, 4H); 1.2 (m, 3H); 1.0 (m, 3H). FDMS m/e 629

Preparation of PFED-18

The phthalamido-blocked compound PFED-14 (0.3 g, 0.57 mmol), trifluoroacetic anhydride (0.12 g, 0.57 mmol) and diisopropylethylamine (0.07 g, 0.57 mmol) were dissolved in 10 mL of THF and the mixture was stirred at room temperature for 24 hours. The reaction mixture was then partitioned between ethyl acetate (100 mL) and brine (100 mL). The organic layer was separated, dried over anhydrous sodium sulfate and concentrated at reduced pressure. The resulting material was chromatographed on silica gel using THF:heptane 2:1 as eluant, which yielded the desired PFED-18.

$^1$H NMR(CDCl$_3$): 8.0–7.6(m, 8H); 5.8 (m, 2H); 5.9 (q, 1H); 3.3 (m, 4H); 1.3 (d, 3H); 1.3 (m, 3H); 1.0 (m 3H). ESMS m/e 620

Preparation of PFED-19

The phthalamido-blocked compound PFED-13 (0.78 g, 1.5 mmol), trifluoroacetic anhydride (0.32 g, 1.5 mmol) and diisopropylethylamine (0.2 g, 1.5 mmol) were dissolved in 10 mL of THF and the mixture was stirred at room temperature for 24 hours. The reaction mixture was then partitioned between ethyl acetate (100 mL) and brine (100 mL) with 10 mL of saturated sodium bicarbonate. The organic layer was separated, washed with 10 mL of brine, dried over anhydrous sodium sulfate and concentrated at reduced pressure. The resulting material was chromatographed on silica gel using THF:heptane 2:1 as eluant, which yielded the desired PFED-19 (0.5 g).

$^1$H NMR(CDCL$_3$): 7.9 (m, 2H); 7.8 (m, 2H); 7.7 (m, 2H); 7.65(m, 2H); 5.8 (s, 2H); 4.45 (s, 2H); 3.3 (m, 4H); 1.15 (m, 3H); 1.05 (m, 3H). ESMS m/e 606

Preparation of PFED-32
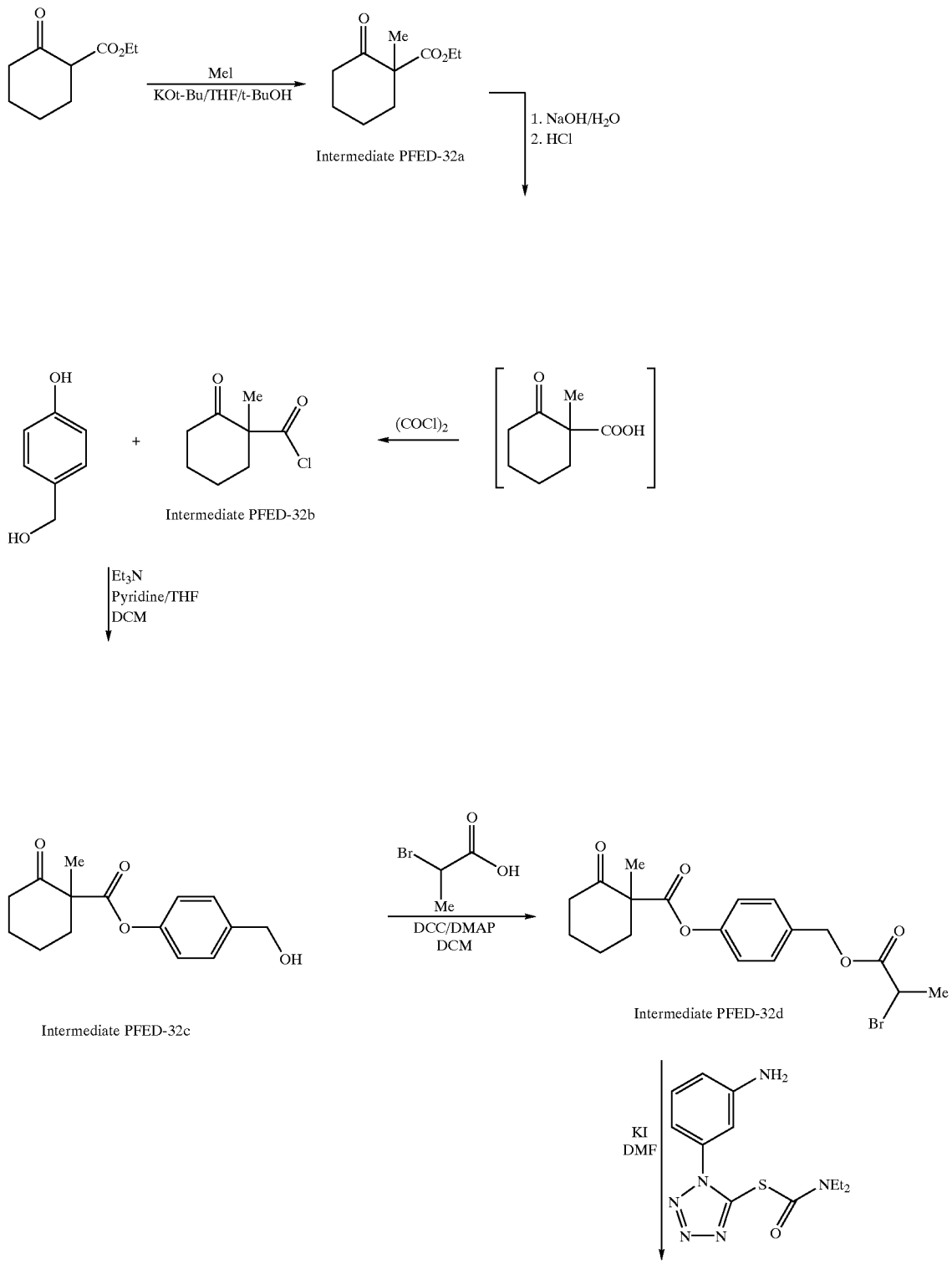
Scheme IV

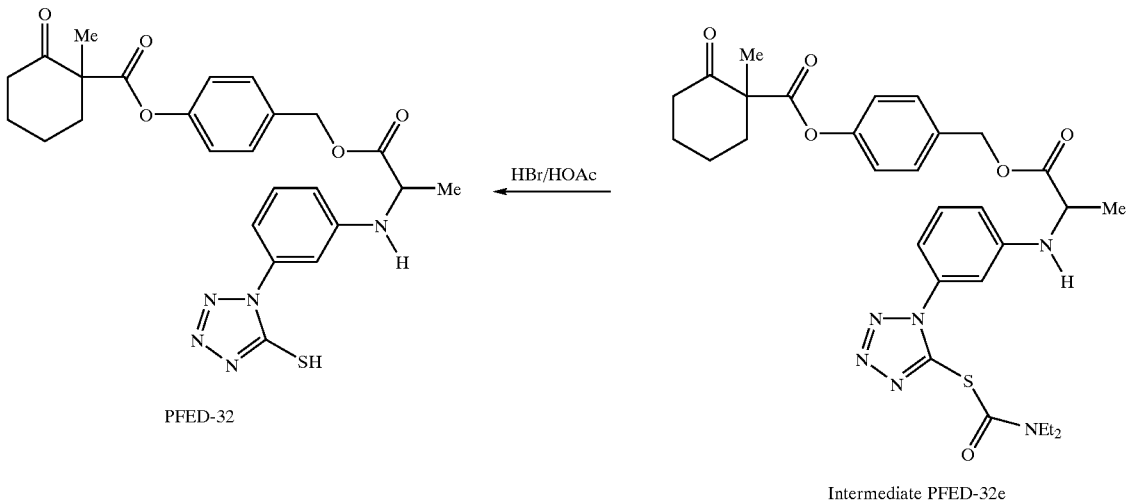

PFED-32 ← HBr/HOAc ── Intermediate PFED-32e

Preparation of Intermediate PFED-32a

Into a one liter flask was placed 68 grams (0.4 mole) of ethyl 2-cyclohexaneonecarboxylate, 60 mL of tetrahydrofuran, and 300 mL of tert-butyl alcohol. The reactants were cooled in an ice bath and 44.8 grams (0.4 mole) of potassium tert-butoxide was added. The ice bath was removed and 113 grams (49.7 mL, 0.8 mole) of iodomethane pre-dissolved in 120 mL of tetrahydrofuran was added through a dropping funnel over 20 minutes. The reaction was stirred at room temperature for 3 hours, then was poured into a 2 L separatory funnel. To the product mixture was added 200 mL of aqueous saturated sodium chloride solution and the organic layer was extracted with 200 mL of diethyl ether. The separated organic layer was washed twice with 200 mL of 0.1 N aqueous sodium hydroxide, twice with 200 mL of 10% aqueous hydrochloric acid, and once with 200 mL of distilled water. The organic layer was dried over magnesium sulfate and concentrated under reduced pressure. The resulting product was dissolved in 150 mL of dichloromethane and washed three times with 100 mL of distilled water to remove residual tert-butyl alcohol. The dichloromethane layer was dried over magnesium sulfate, concentrated to dryness, and placed under vacuum for 12 hours. The weight of tan-brown liquid product was 61.6 grams (0.33 mole, 83.6% yield).

$^1$H NMR(CDCL$_3$): 4.2 (q, 2H); 2.5 (m, 3H); 2.0 (m, 1H); 1.7 (m, 3H); 1.5 (m, 1H); 1.29 (s, 3H); 1.26 (t, 3H).

Preparation Intermediate PFED-32b

Into a 500 mL flask was placed 150 mL of distilled water and 24 grams (0.6 mole) of sodium hydroxide. The mixture was stirred and, after the sodium hydroxide had dissolved, chilled to −5° C. in an ice/ethanol bath. Then, 36.8 grams (0.2 mole) of Intermediate PFED-32a was added dropwise with stirring via a pressure equalized dropping funnel under a nitrogen atmosphere over a period of 15 minutes. The mixture was gradually allowed to warm to room temperature and stirred for 16 hours. The resulting product mixture was chilled to −5° C. in an ice/ethanol bath and carefully acidified to pH about 1 by the dropwise addition of about 50 mL of concentrated hydrochloric acid over about 25 minutes. The resulting milky colored emulsion was poured into a 500 mL separatory funnel while cold and extracted three times with dichloromethane. The dichloromethane layer was dried over magnesium sulfate, concentrated to near dryness under reduced pressure at a temperature of less than 30° C., then dried under vacuum for 30 minutes to afford 28.9 grams of a colorless liquid product which was used in the following step. To the crude acid product obtained above (28.9 grams) in a one liter flask was added 46.8 grams (0.37 mole) of oxalyl chloride. The mixture was placed under a nitrogen atmosphere and stirred at room temperature for 30 minutes, then allowed to stand at room temperature without stirring for 16 hours. The resulting light brown liquid was diluted with 50 mL of dichloromethane and concentrated under reduced pressure at less than 30° C. Treatment with dichloromethane and concentration was repeated twice more. The product was then placed under high vacuum (less than 1 mm Hg) for three hours. The weight of very lightly tan colored liquid product obtained was 27.8 grams (0.16 mole, 80% yield).

$^1$H NMR(CDCL$_3$): 2.64 (m, 3H); 2.10 (m, 1H); 1.8 (m, 3H); 1.6 (m, 1H); 1.44 (s, 3H).

Preparation of Intermediate PFED-32c

Into a one liter flask was placed 19.8 grams (0.16 mole) of 4-hydroxy benzyl alcohol, 160 mL of pyridine, and 40 mL of tetrahydrofuran. To the stirred mixture at room temperature was added 40.2 grams (55.4 mL, 0.4 mole) of triethylamine. The reaction was chilled to −20° C. and a solution of 27.8 grams (0.16 mole) of Intermediate PFED-32b in 160 mL of dichloromethane was added dropwise over 15 minutes while maintaining a temperature of −20° C. The cooling bath was removed and the reaction was allowed to warm to room temperature with stirring for one hour. The product mixture was diluted with 250 mL of dichloromethane, poured into a separatory funnel, and washed once with an aqueous solution composed of 100 mL of 10% hydrochloric acid and 100 mL of saturated sodium chloride, then once with 100 mL of aqueous saturated sodium chloride solution. The organic layer was dried over magnesium sulfate and concentrated under reduced pressure at less than 40° C. to give a thick liquid crude product. This material was re-dissolved in 250 mL of dichloromethane and washed three times with 100 mL of aqueous 10% hydrochloric acid (until a pH of about 2 was obtained for the aqueous wash), then once with 100 mL of distilled water. The organic layer was dried over magnesium sulfate and concentrated to near dryness under reduced pressure at less than 40° C., then placed under high vacuum for one hour. The weight of crude product as a thick liquid was 32.6 grams. Purification by silica gel column chromatography afforded 16.8 grams (64 mmole, 40% yield) of pure product as a colorless thick liquid.

$^1$H NMR(CDCL$_3$): 7.31 (d, 2H); 7.00 (d, 2H); 4.59 (s, 2H); 2.90 (br. s, 1H); 2.60 (m, 3H); 2.06 (m, 1H); 1.82 (m, 3H); 1.61 (m, 1H); 1.46 (s, 3H).

Preparation of Intermediate PFED-32d

To a stirred solution under nitrogen of 4.8 grams (18.3 mmole) of Intermediate PFED-32c, 3.1 grams (20.1 mmole) of 2-bromopropionic acid and 50 mL of dichloromethane in a 250 mL flask was added 0.73 grams (6 mmole) of 4-dimethylaminopyridine. Then, a solution of 4.14 grams (20.1 mmole) of dicyclohexylcarbodiimide in 20 mL of dichloromethane was added dropwise over 10 minutes. The reaction was then stirred at room temperature for 16 hours. The product mixture was filtered and the collected white solid discarded. The filtrate was concentrated under reduced pressure to a light tan thick liquid. The product was isolated by silica gel column chromatography to afford 5.0 grams (12.6 mmole, 70% yield) of a clear colorless liquid.

$^1$H NMR(CDCL$_3$): 7.39 (d, 2H); 7.11 (d, 2H); 5.18 (br. s, 2H), 4.41 (q, 1H); 2.58 (m, 3H); 2.09 (m, 1H); 1.84 (m+s, 3H+3H); 1.62 (m, 1H); 1.48 (s, 3H).

Preparation of Intermediate PFED-32e

Into a 100 mL flask was placed a solution of 5.0 grams (12.6 mmole) of Intermediate PFED-32d in 30 mL of dimethylformamide. With stirring at room temperature under nitrogen 4.15 grams (25 mmole) of potassium iodide was added. To the resulting cloudy white slurry with stirring was added all at once 4.38 grams (15 mmole) of S-[1-(3-aminophenyl)-1H-tetrazol-5-yl]carbamothioic acid diethyl ester. The reaction was stirred at room temperature for 5 minutes then heated to 70° C. and stirred at this temperature for 18 hours. The crude product mixture was removed from the oil bath and concentrated to a thick dark oil under reduced pressure at 60° C. The crude product was dissolved in 100 mL of dichloromethane and poured into a separatory funnel containing 250 mL of distilled water. The mixture was shaken, separated, and the organic layer collected. The aqueous layer was extracted four times with 50 mL of dichloromethane then the aqueous layer was discarded. The combined organic phases were placed in a separatory funnel and washed five times with 50 mL of distilled water. The organic layer was dried over magnesium sulfate, concentrated to near dryness under reduced pressure then placed under high vacuum for 16 hrs. The weight of crude product was 10.3 grams. The pure product was isolated by silica gel column chromatography to afford 3.3 grams (5.4 mmole, 43% yield) of a white amorphous semi-solid. ESMS$^+$: m/e 609

$^1$H NMR(CDCL$_3$): 7.33 (m, 3H); 7.07 (d, 2H); 6.89 (d, 1H); 6.76 (m, 2H); 5.15 (br.s, 2H); 4.59 (br.s, 1H); 4.18 (q, 1H); 3.31 (br.q, 4H); 2.59 (m, 3H); 2.08 (m, 1H); 1.83 (m, 3H); 1.63 (m, 1H); 1.50 (d, 3H); 1.48 (s, 3H); 1.21 (br.t, 3H); 104 (br.t, 3H).

Preparation of PEED-32

Into a 50 mL flask was placed 1.5 grams (2.4 mmole) of Intermediate PFED-32e and 10 mL of neat 30% hydrobromic acid in acetic acid. The reaction was stirred at room temperature for 30 minutes. Analysis by high pressure liquid chromatography showed nearly quantitative consumption of the starting material after this time. The crude product mixture was poured into 200 mL of rapidly stirring distilled water resulting in the formation of a white semi-solid precipitate. After stirring for 30 minutes at room temperature, the product was isolated by filtration and dried at room temperature under high vacuum to afford 1.2 grams of crude product which was shown to be about 95% pure by high pressure chromatography analysis. After column chromatography, 0.72 grams (1.4 mmole, 59% yield) of pure PFED-32 was obtained as a white amorphous semi-solid. ESMS$^+$: m/e 510

$^1$H NMR(CDCL$_3$): 7.35–7.17 (m, 5H); 7.07 (d, 2H); 6.89 (d, 1H); 5.20 (d of d, 2H); 4.22 (q, 1H); 2.60 (m, 3H); 2.08 (m, 1H); 1.82 (m, 3H); 1.66 (m, 1H) (d, 3H); 1.50 (s, 3H).

Examples illustrating the beneficial use of these protected fragmentable electron donating sensitizer compounds in silver halide emulsions are given in the following

EXAMPLE 1

An AgBrI tabular silver halide emulsion (Emulsion T-1) was prepared containing 4.05% total I distributed such that the central portion of the emulsion grains contained 1.5% I and the perimeter area contained substantially higher I as described by Chang et. al., U.S. Pat. No. 5,314,793. The emulsion grains had an average thickness of 0.112 μm and average circular diameter of 1.25 μm. Emulsion T-1 was precipitated using deionized gelatin. The emulsion was sulfur sensitized by adding 1,3-dicarboxymethyl-1,3-dimethyl-2-thiourea at 40° C.; the temperature was then raised to 60° C. at a rate of 5° C./3 min and the emulsions held for 20 min before cooling to 40° C. The amount of the sulfur sensitizing compound used was $8.5 \times 10^{-6}$ mole/mole Ag. Blue (D-I) or green (D-II) spectral sensitizing dye was then added at 0.91 mmole/mole Ag for coatings containing the dye D-I and 0.86 mmole/mole Ag for coatings containing the dye D-II. The antifoggant, 2,4-disulfocatechcol (HB3) at a concentration of $13 \times 10^{-3}$ mole/mole Ag was also added. The chemically and spectrally sensitized emulsion was then used to prepare the experimental coating variations indicated in Example Table I.

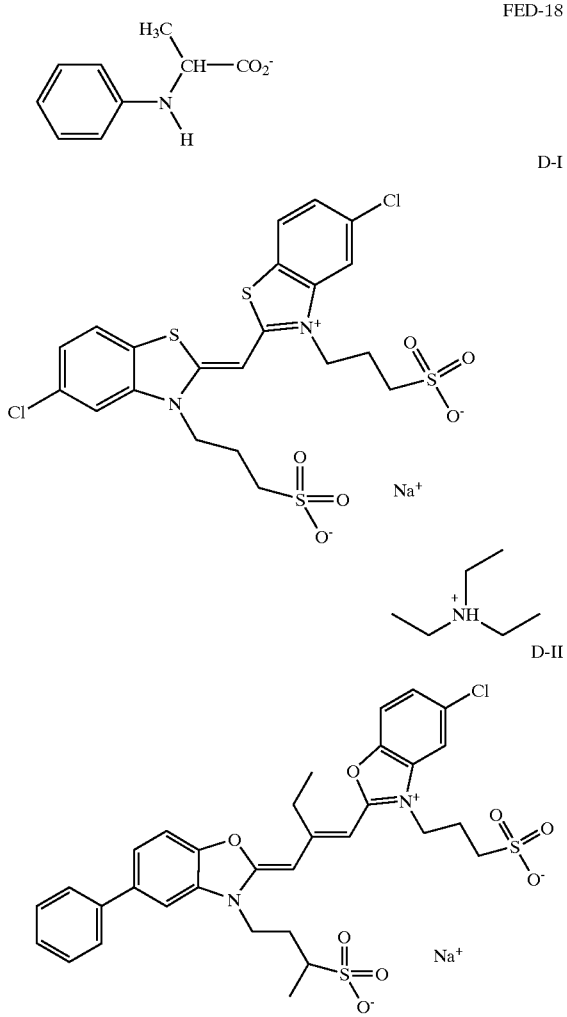

The protected fragmentable electron donating sensitizer compounds (PFED) were dissolved in methanol and added to the emulsion at the relative concentrations indicated in Example Table I. In some experiments the parent FED compound (FED 18) that contains no protecting group A was added as a comparison compound. At the time of PFED sensitizer addition, the emulsion melts had a VAg of 85–90 mV and a pH of 6.0. Additional water, gelatin, and surfactant were then added to the emulsion melts to give a final emulsion melt that contained 216 grams of gel per mole of silver. These emulsion melts were coated onto an acetate film base at 1.61 g/m$^2$ of Ag with gelatin at 3.22 g/m$^2$. The coatings were prepared with a protective overcoat which contained gelatin at 1.08 g/m$^2$, coating surfactants, and a bisvinylsulfonylmethyl ether as a gelatin hardening agent.

For photographic evaluation, each of the coating strips was exposed for 0.1 sec to a 365 nm emission line of a Hg lamp filtered through a Kodak Wratten filter number 18A and a step wedge ranging in density from 0 to 4 density units in 0.2 density steps. $S_{365}$, relative sensitivity at 365 nm, was evaluated at a density of 0.15 units above fog. Relative sensitivity for this exposure was set equal to 100 for the control dyed emulsion coating with no PFED (or FED) compound added (test no. 1).

Additional testing was carried out to determine the response of the coatings to a spectral exposure. The dyed coating strips were exposed for 0.1 sec to a 3000 K color temperature tungsten lamp filtered to give an effective color temperature of 5500 K and further filtered through a Kodak Wratten filter number 2B and a step wedge ranging in density from 0 to 4 density units in 0.2 density steps. This filter passes only light of wavelengths longer than 400 nm, thus giving light absorbed mainly by the sensitizing dye. The exposed filmstrips were developed for 6 min in Kodak Rapid X-ray Developer (KRX). $S_{WR2B}$, relative sensitivity for this Kodak Wratten filter 2B exposure, was evaluated at a density of 0.15 units above fog. The relative sensitivity for this spectral exposure was set equal to 100 for the control dyed coating with no PFED (or FED) compound added (tests no. 1 and no. 14)).

TABLE I

Speed and fog results for PFED compounds on Emulsion T-1

| Test No. | Sens. Dye | Compound Added | Amount of Compound added (mmol/mol Ag) | $S_{365}$ | Fog | $S_{W2B}$ | Remarks |
|---|---|---|---|---|---|---|---|
| 1 | D-I | none | none | 100 | 0.04 | 100 | control |
| 2 | D-I | FED-18 | 4.4 | 135 | 0.04 | 126 | comparison |
| 3 | D-I | FED-18 | 14 | 200 | 0.08 | 182 | comparison |
| 4 | D-I | FED-18 | 44 | 191 | 0.11 | 191 | comparison |
| 5 | D-I | PFED-1 | 4.4 | 148 | 0.03 | 148 | invention |
| 6 | D-I | PFED-1 | 14 | 166 | 0.04 | 155 | invention |
| 7 | D-I | PFED-20 | 14 | 155 | 0.04 | 148 | invention |
| 8 | D-I | PFED-20 | 44 | 162 | 0.05 | 155 | invention |
| 9 | D-I | PFED-21 | 4.4 | 110 | 0.03 | 105 | invention |
| 10 | D-I | PFED-21 | 14 | 100 | 0.04 | 94 | invention |
| 11 | D-I | PFED-22 | 14 | 107 | 0.03 | 100 | invention |
| 12 | D-I | PFED-22 | 44 | 110 | 0.03 | 102 | invention |
| 13 | D-I | PFED-23 | 44 | 123 | 0.03 | 118 | invention |
| 14 | D-II | none | none | 100 | 0.08 | 100 | control |
| 15 | D-II | FED-18 | 0.44 | 155 | 0.13 | 159 | comparison |
| 16 | D-II | FED-18 | 1.4 | 135 | 0.20 | 138 | comparison |
| 17 | D-II | FED-18 | 4.4 | 166 | 0.25 | 178 | comparison |
| 18 | D-II | PFED-1 | 0.44 | 138 | 0.09 | 145 | invention |

TABLE I-continued

Speed and fog results for PFED compounds on Emulsion T-1

| Test No. | Sens. Dye | Compound Added | Amount of Compound added (mmol/mol Ag) | Photographic Sensitivity | | | Remarks |
|---|---|---|---|---|---|---|---|
| | | | | $S_{365}$ | Fog | $S_{W2B}$ | |
| 19 | D-II | PFED-1  | 1.4  | 155 | 0.13 | 166 | invention |
| 20 | D-II | PFED-20 | 1.4  | 151 | 0.11 | 151 | invention |
| 21 | D-II | PFED-20 | 4.4  | 155 | 0.23 | 155 | invention |
| 22 | D-II | PFED-21 | 0.44 | 135 | 0.08 | 129 | invention |
| 23 | D-II | PFED-21 | 1.4  | 129 | 0.07 | 126 | invention |
| 24 | D-II | PFED-22 | 4.4  | 120 | 0.07 | 112 | invention |
| 25 | D-II | PFED-22 | 14   | 123 | 0.07 | 115 | invention |
| 26 | D-II | PFED-23 | 1.4  | 112 | 0.07 | 112 | invention |
| 27 | D-II | PFED-23 | 4.4  | 126 | 0.08 | 120 | invention |

The data in Example Table I demonstrate that each of the protected fragmentable electron donating sensitizer compounds PFED-1, PFED-20, PFED-21, PFED-22, and PFED-23 provide an increase in the photographic sensitivities of the silver halide emulsion. Improved sensitivity, up to a factor of about 1.6, is observed for emulsions given either the 365 nm exposure or a spectral exposure $S_{WR2B}$ in the region of light absorption by the sensitizing dye. The observed increases in emulsion performance found for the PFED compounds are, for most PFED compounds, improved relative to that obtained for the comparison compound FED-18, which does not bear a protecting group. The comparison compound FED-18 does improve the emulsion sensitivity, however, the sensitivity increases are accompanied by increases in fog, particularly for the emulsion containing the green sensitizing dye D-II. The protected fragmentable electron donor compounds give sensitivity increases that are similar to FED-18 but with less unwanted fog.

EXAMPLE 2

The tabular silver halide Emulsion T-1 was prepared as described in example 1 except that the antifoggant HB-3 was not added to the emulsion. Blue (D-I) or green (D-II) spectral sensitizing dye and the protected fragmentable electron donating sensitizer compound PFED-1 (or comparison compound FED-16) were then added to the emulsion and coatings prepared and tested as described in Example I.

Additional testing was performed to determine if the presence of the inventive compound improved the storage characteristics of the coated emulsions. The coated emulsions (tests 1–14) were incubated in the dark for 1 week in a controlled environment of 120° C. and 50% relative humidity. The incubated coatings were then exposed and chemically processed as described as described in Example I. Changes in the amount of fog are reported relative to the similar coated emulsion that were incubated in the dark at 0° C.

The data in Example Table II demonstrate an increase in the photographic sensitivities for emulsions containing the protected fragmentable electron donating sensitizer compounds PFED-1. Improved sensitivity is observed for the 365 nm exposure and the spectral exposure $S_{WR2B}$ for all examples which contained the PFED, and the sensitivity improvement increased as the compound concentration was increased. Sensitivity increases up to a factor of 1.6× are observed.

Increases in photographic sensitivity are also found for the comparison compound FED-18, however, the sensitivity increases are accompanied by significant increases in fog, particularly for the emulsion containing the green sensitizing dye D-II. In comparison, similar sensitivity increases with much less fog are obtained for the emulsions containing the protected fragmentable electron donor compound PFED-1. In addition, the coatings containing the PFED-1 show less fog growth during storage at 120° C. than those coatings containing FED-18.

EXAMPLE TABLE II

Speed and fog results for PFED 1 on Emulsion T-1

| Test No. | Sens. Dye | Compound Added | Amount of Compound added (mmol/mol Ag) | Photographic Sensitivity | | | Fog Growth on Storage | Remarks |
|---|---|---|---|---|---|---|---|---|
| | | | | $S_{365}$ | Fog | $S_{W2B}$ | | |
| 1  | D-I  | none   | none | 100 | 0.04 | 100 | −0.01 | control |
| 2  | D-I  | FED-18 | 1.4  | 170 | 0.06 | 162 | 0.00  | comparison |
| 3  | D-I  | FED-18 | 4.4  | 186 | 0.08 | 186 | 0.02  | comparison |
| 4  | D-I  | FED-18 | 14   | 200 | 0.11 | 195 | 0.00  | comparison |
| 5  | D-I  | PFED-1 | 1.4  | 135 | 0.04 | 132 | 0.00  | invention |
| 6  | D-I  | PFED-1 | 4.4  | 148 | 0.05 | 145 | 0.00  | invention |
| 7  | D-I  | PFED-1 | 14   | 166 | 0.05 | 159 | 0.00  | invention |
| 8  | D-II | none   | none | 100 | 0.08 | 100 | 0.00  | control |
| 9  | D-II | FED-18 | 1.4  | 129 | 0.20 | 132 | 0.02  | comparison |
| 10 | D-II | FED-18 | 4.4  | 123 | 0.37 | 138 | 0.14  | comparison |
| 11 | D-II | FED-18 | 14   | 155 | 0.39 | 148 | 0.25  | comparison |

EXAMPLE TABLE II-continued

Speed and fog results for PFED 1 on Emulsion T-1

| Test No. | Sens. Dye | Compound Added | Amount of Compound added (mmol/mol Ag) | Photographic Sensitivity $S_{365}$ | Fog | $S_{W2B}$ | Fog Growth on Storage | Remarks |
|---|---|---|---|---|---|---|---|---|
| 12 | D-II | PFED-1 | 1.4 | 126 | 0.10 | 123 | 0.00 | invention |
| 13 | D-II | PFED-1 | 4.4 | 145 | 0.14 | 138 | 0.03 | invention |
| 14 | D-II | PFED-1 | 14 | 151 | 0.23 | 162 | 0.13 | invention |

EXAMPLE 3

A monodisperse AgBrI tabular silver halide emulsion T-2 containing 3.6% total I was prepared according to the procedures described in Fenton et al. U.S. Pat. No. 5,476,760 in a manner such that the central portion of the emulsion grains contained essentially no I and the I was concentrated around the grain perimeter but was higher at the edges than at the corners. The emulsion grains had an average thickness of 0.12 μm and an average circular diameter of 2.7 μm. This emulsion T-2 was optimally chemically and spectrally sensitized by adding NaSCN, $0.77 \times 10^{-3}$ mole/mole Ag of the green sensitizing dye D-II, $0.17 \times 10^{-3}$ mole/mole Ag of the green sensitizing dye D-IV, $Na_3Au(S_2O_3)_2 \cdot 2H_2O$, $Na_2S_2O_3 \cdot 5H_2O$, and a benzothiazolium finish modifier and then subjecting the emulsion to a heat cycle to 65° C. The antifoggant and stabilizer tetraazaindene at a concentration of 1.00 gm/mole Ag was added to the emulsion melt after the chemical sensitization procedure. The antifoggant 2,4-disulfocatechcol (HB3) at a concentration of $13 \times 10^{-3}$ mole/mole Ag was also added. Various protected fragmentable electron donating sensitizer compounds and a comparison fragmentable electron donating sensitizer compound as listed in Table III were added to the emulsion after the addition of HB3. The melts were prepared for coating by adding additional water, deionized gelatin, and coating surfactants. Coatings were prepared by combining the emulsion melts with a melt containing deionized gelatin and an aqueous dispersion of the cyan-forming color coupler CC-1 and coating the resulting mixture on acetate support. The final coatings contained Ag at 0.81 g/m², coupler at 1.61 g/m², and gelatin at 3.22 g/m². The coatings were overcoated with a protective layer containing gelatin at 1.08 g/m², coating surfactants, and a bisvinylsulfonylmethyl ether as a gelatin hardening agent.

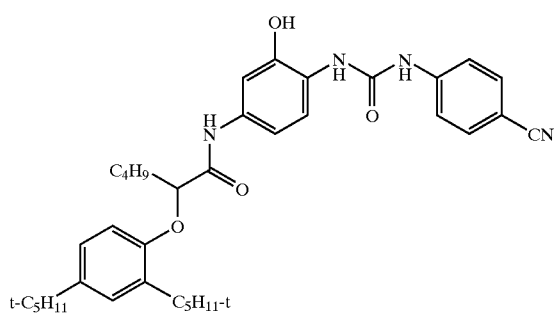

CC-1

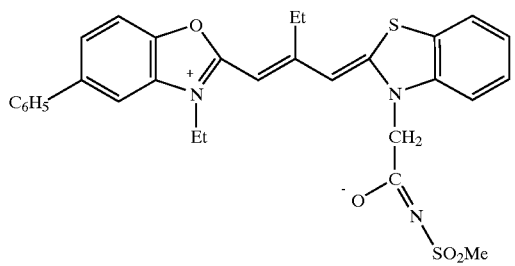

D-III $S_{365}$, relative sensitivity at 365 nm, and $S_{WR2B}$, relative sensitivity for the Kodak Wratten 2B filtered exposure, were evaluated as described in Example 1, except that the exposure time used was 0.01 s, and the exposed film strips were developed for 3¼ minutes in Kodak C-41 color developer. $S_{WR2B}$ and $S_{365}$ were evaluated at a cyan density of 0.20 units above fog. Relative sensitivity for both exposures was set equal to 100 for the control emulsion coating with no fragmentable electron donating sensitizer agent added (test no. 1).

TABLE III

Speed and fog results for combinations of PFED and green dye sensitized emulsion T-2, color format

| Test No. | Compound Added | Amount of Compound added (mmol/mol Ag) | Photographic Sensitivity $S_{365}$ | Fog | $S_{W2B}$ | Remarks |
|---|---|---|---|---|---|---|
| 1 | none | none | 100 | 0.05 | 100 | control |
| 2 | FED-18 | 0.044 | 112 | 0.09 | 115 | comparison |
| 3 | FED-18 | 0.14 | 120 | 0.16 | 126 | comparison |
| 4 | PFED-1 | 0.44 | 115 | 0.09 | 120 | invention |
| 5 | PFED-1 | 1.4 | 123 | 0.18 | 129 | invention |
| 6 | PFED-15 | 0.14 | 117 | 0.08 | 123 | invention |
| 7 | PFED-15 | 0.44 | 155 | 0.25 | 148 | invention |
| 8 | PFED-20 | 0.44 | 105 | 0.05 | 105 | invention |
| 9 | PFED-20 | 1.4 | 117 | 0.06 | 115 | invention |

The data in Table III demonstrate that the PFED compounds, when added to the emulsion at their optimal concentrations, can give increases in sensitivity for this fully sensitized, green-dyed emulsion with only minimal increases in fresh fog. Sensitivity increases of up to 1.2× are obtained with less than 0.05 increase in fresh fog. In contrast, for the comparison compound FED-18 (which does not have a protecting group), a 1.2× sensitivity increase is accompanied by an 0.11 increase in fog.

EXAMPLE 4

Emulsion T-2 was prepared and sensitized as described in Example 3. After addition of the antifoggant HB-3, protected fragmentable electron donating sensitizer compounds PFED-14 and PFED-18 were added to the emulsion melts at Ad7; the levels indicated in Table IV. These PFED compounds are examples of protected fragmentable electron donating sensitizer compounds containing a moiety that promotes adsorption to the silver halide surface. The emulsion melts were then used to prepare color format coatings as described in Example 3 and the resulting coatings were exposed and processed as described in Example 3. The data contained in Table IV indicates that both of these silver halide absorptive PFED compounds gave useful increases in the sensitivity of this fully sensitized, green dyed emulsion with only minimal increases in fresh fog.

TABLE IV

Speed and fog results for combinations of PFED and green dye sensitized emulsion T-2, color format

| Test No. | Compound Added | Amount of Compound added (mmol/mol Ag) | Photographic Sensitivity $S_{365}$ | Fog | $S_{W2B}$ | Remarks |
|---|---|---|---|---|---|---|
| 1 | none | none | 100 | 0.05 | 100 | control |
| 2 | PFED-14 | 0.014 | 105 | 0.08 | 102 | invention |
| 3 | PFED-14 | 0.044 | 112 | 0.13 | 112 | invention |
| 4 | PFED-18 | 0.14 | 110 | 0.08 | 110 | invention |
| 5 | PFED-18 | 0.28 | 120 | 0.13 | 120 | invention |

The invention has been described in detail with particular reference to certain preferred embodiments thereof, but it will be understood that variations and modifications can be effected within the spirit and scope of the invention.

What is claimed is:

1. A photographic element comprising at least one silver halide emulsion layer in which the silver halide is sensitized with a protected fragmentable electron donor compound of the formula (a), (b) or (c):

  (a)

  (b)

  (c)

wherein Δ is protective group that is eliminated during development of the photographic element, t is a timing group, m is an integer from 0 to 3, and XY' is a fragmentable electron donor moiety in which X is an electron donor group and Y' is a leaving proton H or a leaving group Y, with the proviso that if Y' is a proton, a base, $\beta^-$, is present in the emulsion or is covalently linked directly or indirectly to X, and wherein:

1) X—Y' has an oxidation potential between 0 and about 1.4 V;
2) the oxidized form of X—Y' undergoes a bond cleavage reaction to give the radical X˙ and the leaving fragment Y'; and
3) the radical X˙ has an oxidation potential $\leq -0.7$ V.

2. A photographic element according to claim 1, wherein Y' is a leaving group Y.

3. A photographic element according to claim 1, wherein Y' is a proton, the compound is of formula (a) and a base, β, is covalently linked to X.

4. A photographic element according to claim 1, wherein the group represented by Δ is a group capable of cleaving on hydrolysis.

5. A photographic element according to claim 4, wherein the group represented by Δ is an acyl group, sulfonyl group, sulfonyl group, or aminomethyl group.

6. A photographic element according to claim 1, wherein the group represented by Δ is a group capable of cleaving on reverse Michael addition reaction.

7. A photographic element according to claim 6, wherein the group represented by Δ is 2-cyanoethyl group, 2-acylethyl group, 2-sulfonylethyl group, 2-carbamoylethyl group or pyrrolidine-2,5-3-yl group.

8. A photographic element according to claim 1, wherein the group represented by Δ is a group capable of cleaving on addition-release reaction.

9. A photographic element according to claim 8, wherein the group represented by Δ is a uracyl group, 2-cyclohexanone-3-yl group, maleinimido-3-yl group, 2-alkoxycaronylethenyl group, or 2-acylethenyl group.

10. A photographic element according to claim 1, wherein the group represented by Δ is a group capable of cleaving on intramolecular electron transfer reaction.

11. A photographic element according to claim 10, wherein the group represented by Δ is a quinonemethide production cleaving group.

12. A photographic element according to claim 1, wherein the group represented by Δ is a group capable of cleaving on intramolecular nucleophilic substitution reaction.

13. A photographic element according to claim 12, wherein the group represented by Δ is 3-acylpropanoyl group or 2-acyl-2,2-dialkylacetyl group.

14. A photographic element according to claim 1, wherein the group represented by Δ is a group blocked with a phthalide group, a saccharin group or an imidomethyl group.

15. A photographic element according to claim 1, wherein $m \leq 1$ and the group represented by t is a group using a cleavage reaction of hemiacetal.

16. A photographic element according to claim 1, wherein $m \leq 1$ and the group represented by t is a group causing a cleavage reaction using an intramolecular nucleophilic substitution reaction.

17. A photographic element according to claim 1, wherein $m \leq 1$ and the group represented by t is a group causing a cleavage reaction using an electron transfer reaction along a conjugated system.

18. A photographic element according to claim 1, wherein $m \leq 1$ and the group represented by t is a group using a cleavage reaction by hydrolysis of an ester.

19. A photographic element according to claim 1, wherein $m \leq 1$ and the group represented by t is a group using a cleavage reaction of iminoacetal.

20. A photographic element according to claim 1, wherein X is of structure (I):

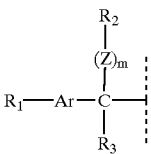  (I)

$R_1 = R$, carboxyl, amide, sulfonamide, halogen, $NR_2$, $(OH)_n$, $(OR')_n$, or $(SR)_n$;
R'=alkyl or substituted alkyl group;
n=1–3;

$R_2$=R, or Ar';

$R_3$=R, or Ar';

$R_2$ and $R_3$ together can form a 5- to 8-membered ring wherein:

m=0, or 1;

Z=O, S, Se, or Te;

$R_2$ and Ar can be linked to form a 5- to 8-membered ring;

$R_3$ and Ar can be linked to form a 5- to 8-membered ring;

Ar'=aryl group or heterocyclic group; and

R=a hydrogen atom or an unsubstituted or substituted alkyl group.

21. A photographic element according to claim 20, wherein the compound of Structure (I) is selected from:

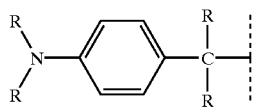
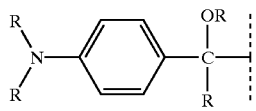
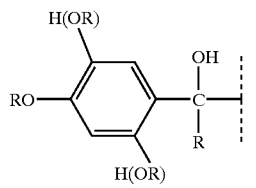
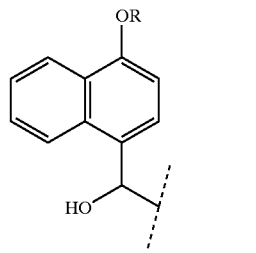
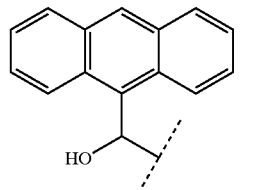
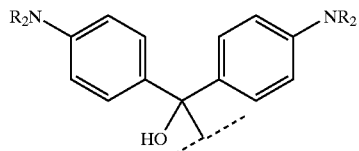
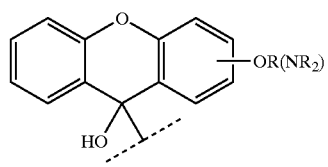
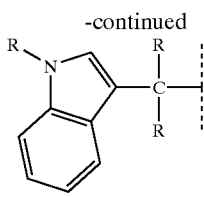
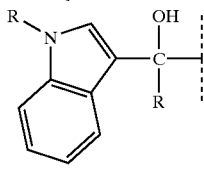
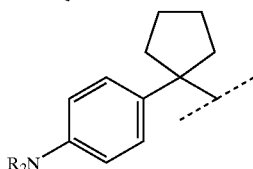
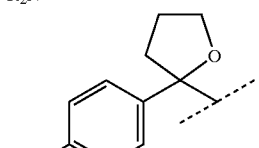
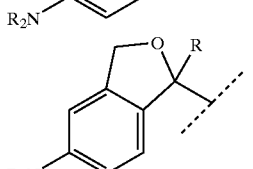

and wherein each R is independently a hydrogen atom or a substituted or unsubstituted alkyl group.

22. A photographic element according to claim 1, wherein X is a compound of structure (II):

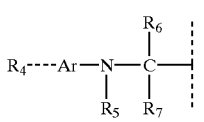

(II)

wherein:

Ar=aryl group or heterocyclic group $R_4$=a substituent having a Hammett sigma value of −1 to +1, $R_5$=R or Ar'

$R_6$ and $R_7$=R or Ar'

$R_5$ and Ar= can be linked to form a 5- to 8-membered ring;

$R_6$ and Ar= can be linked to form a 5- to 8-membered ring (in which case, $R_6$ can be a hetero atom);

$R_5$ and $R_6$ can be linked to form a 5- to 8-membered ring;

$R_6$ and $R_7$ can be linked to form a 5- to 8-membered ring;

Ar'=aryl group or heterocyclic group; and

R=hydrogen atom or an unsubstituted or substituted alkyl group.

23. A photographic element according to claim 22, wherein X is selected from:

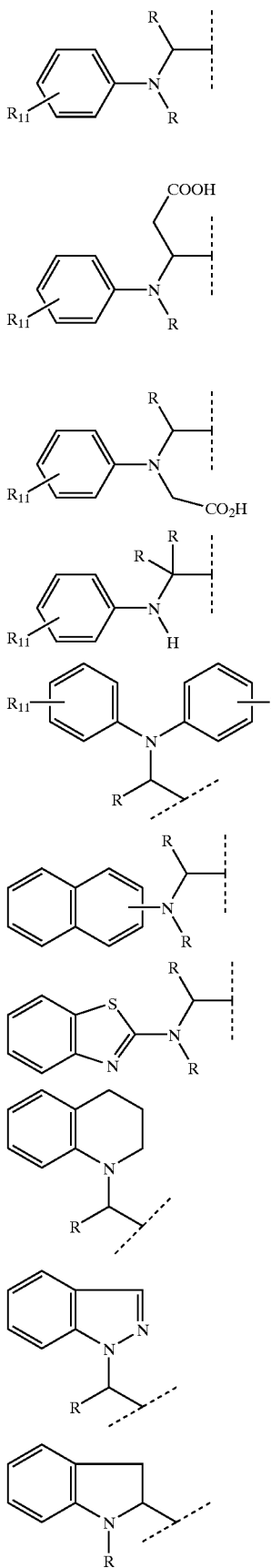

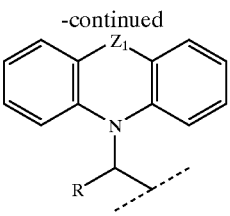

and

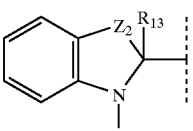

$R_{11}$ and $R_{12}$ = {H, alkyl, alkoxy, alkylthio, halo, carbomoyl, carboxyl, amido, formyl, sulfonyl, sulfonamido, or nitrile}

$Z_1$ = a covalent bond, S, O, Se, NR, $CR_2$, CR=CR, or $CH_2CH_2$;

$Z_2$ = S, O, Se, NR, $CR_2$, or CR=CR;

$R_{13}$ = alkyl, substituted alkyl or aryl; and $R_{14}$ = H, alkyl substituted alkyl or aryl.

24. A photographic element according to claim 1, wherein X is a compound of structure (II):

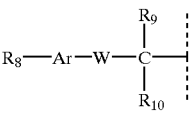

(III)

wherein:

W = O, S, or Se;

Ar = aryl group or heterocyclic group;

$R_8$ = R, carboxyl, $NR_2$, $(OR)_n$, or $(SR)_n$ (n=1–3);

$R_9$ and $R_{10}$ = R, or Ar';

$R_9$ and Ar= can be linked to form a 5- to 8-membered ring;

Ar' = aryl group or heterocyclic group; and

R = a hydrogen atom or an unsubstituted or substituted alkyl group.

25. A photographic element according to claim 24, wherein X is selected from:

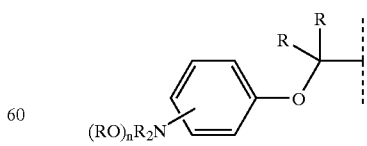

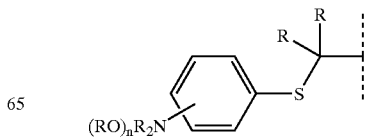

-continued

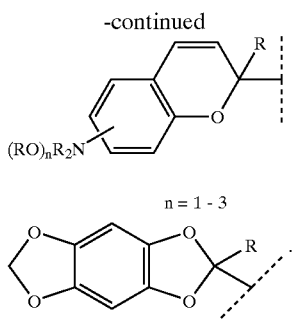

n = 1 - 3

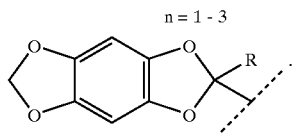

26. A photographic element according to claim 1, wherein X is of structure (IV):

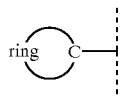 (IV)

wherein:

"ring" represents a substituted or unsubstituted 5-, 6- or 7-membered unsaturated ring.

27. A photographic element according to claim 26, wherein X is selected from:

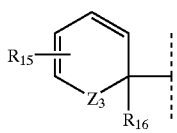

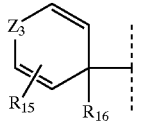 and

$Z_3$=O, S, Se, or NR $R_{15}$=R, OR, or $NR_2$ $R_{16}$=alkyl, or substituted alkyl.

28. A photographic element according to claim 1, wherein Y' is:

(1) X', where X' is an X group as defined in structures I–IV and may be the same as or different from the X group to which it is attached (2)

—COO⁻

(3)

—M(R')$_3$ where M = Si, Sn or Ge; and R' = alkyl or subsituted alkyl

-continued (4)

—B⁻(Ar″)$_3$ where Ar″ = aryl or substituted aryl (5)

—H.

29. A photographic element according to claim 1, wherein the compound of formula (a), (b) or (c) is a compound of the structure:

structure

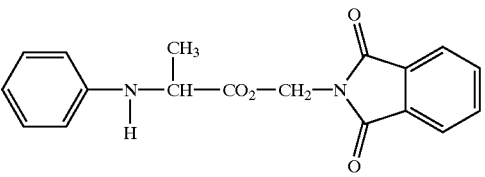

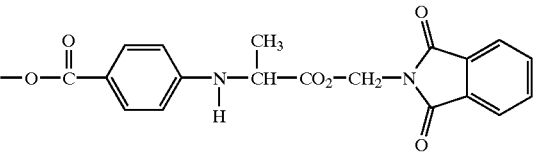

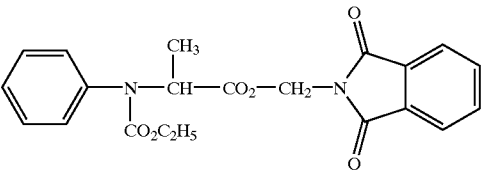

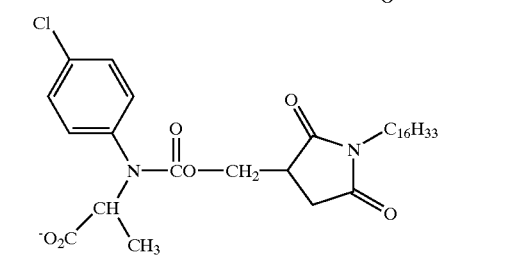

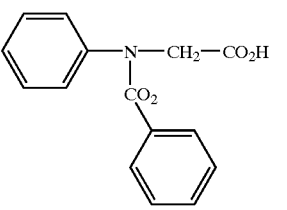

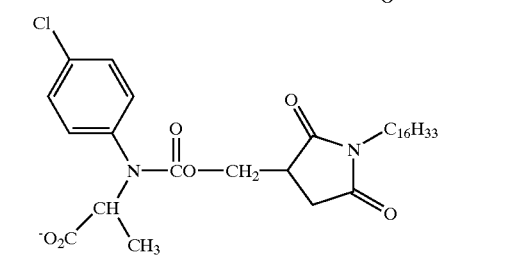

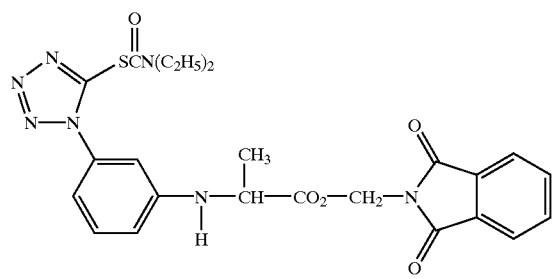
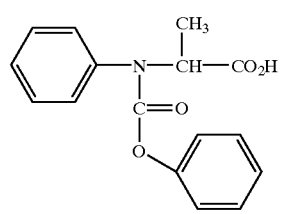
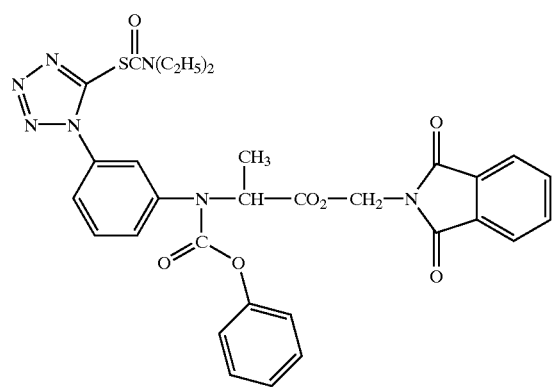
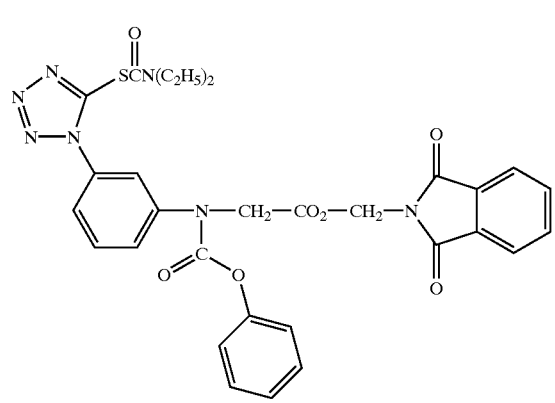
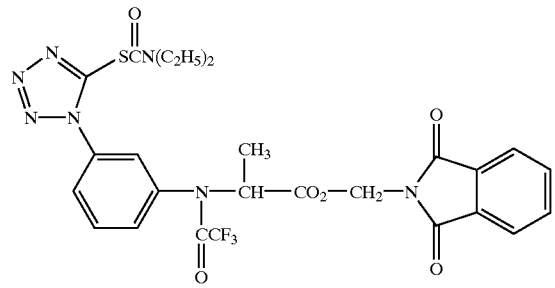
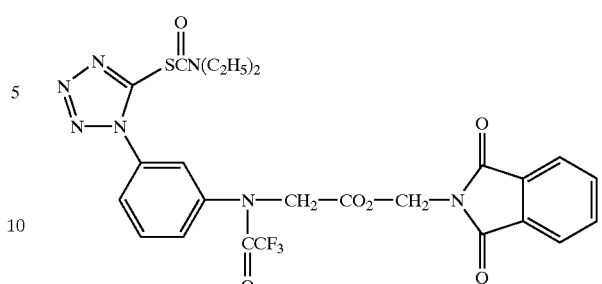
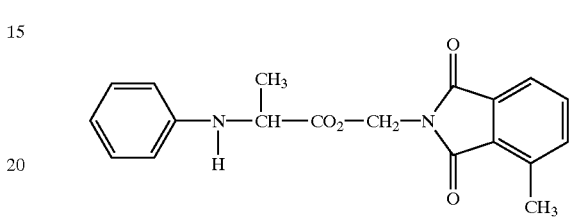
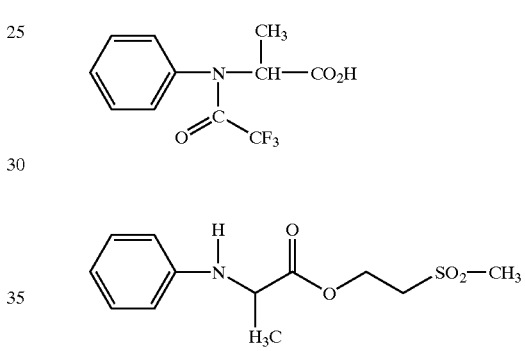
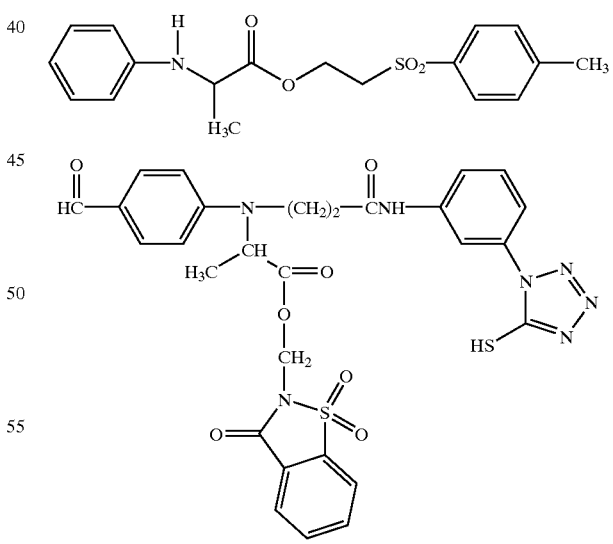
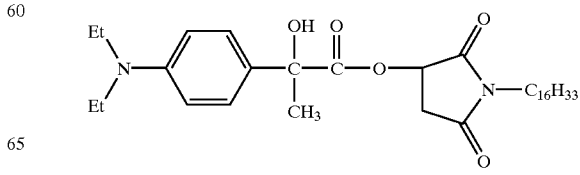

-continued

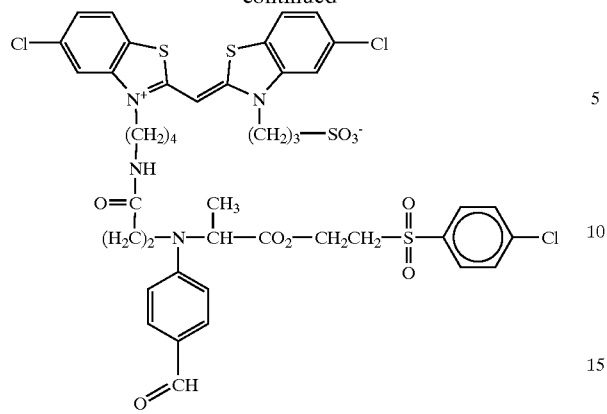

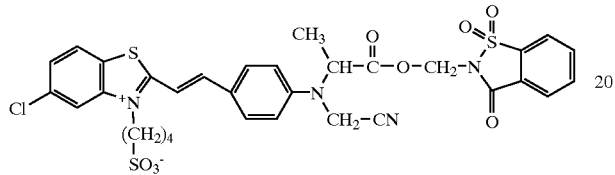

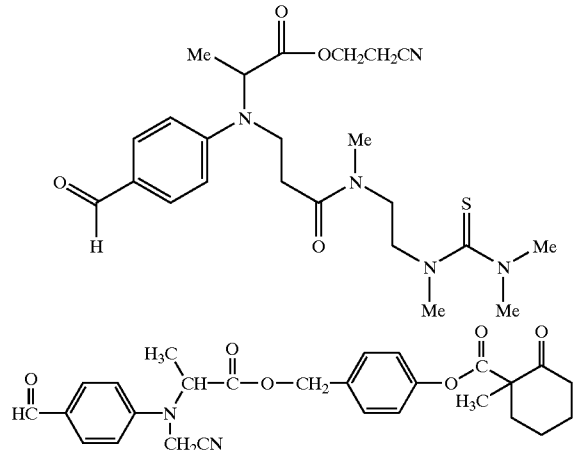

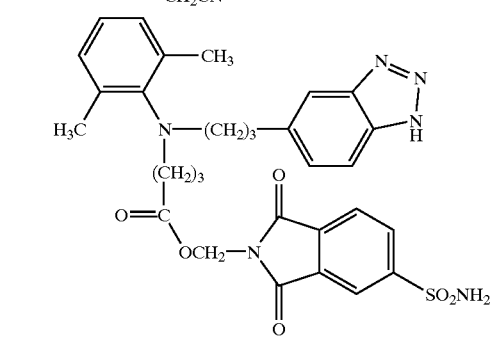

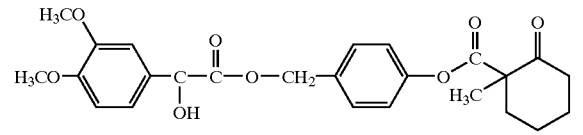

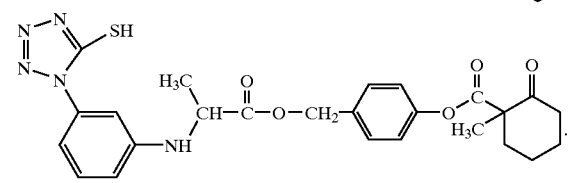

30. A compound of formula:

$$\Delta\text{-(t)}_m\text{-XY'}$$

wherein:

Δ is protective group that is eliminated during development t is a timing group, m is an integer from 0 to 3, XY' is a fragmentable electron donor moiety wherein:
1) X is an electron donor group
2) y' is a leaving proton H or a leaving group Y
3) X—Y' has an oxidation potential between 0 and about 1.4 V
4) the oxidized form of X—Y' undergoes a bond cleavage reaction to give the radical X• and the leaving fragment Y'; and
5) the radical X• has an oxidation potential $\leq -0.7$V.

31. A compound of formula:

$$\text{XY'-(t)}_m\text{-}\Delta$$

wherein:

Δ is protective group that is eliminated during development t is a timing group, m is an integer from 0 to 3, XY' is a fragmentable electron donor moiety wherein:
1) X is an electron donor group
2) Y' is a leaving proton H or a leaving group Y
3) X—Y' has an oxidation potential between 0 and about 1.4 V
4) the oxidized form of X—Y' undergoes a bond cleavage reaction to give the radical X• and the leaving fragment Y'; and
5) the radical X• has an oxidation potential $\leq -0.7$V.

32. A compound of formula:

$$\Delta\text{-(t)}_m\text{-XY'-(t)}_m\text{-}\Delta$$

wherein:

Δ is protective group that is eliminated during development t is a timing group, m is an integer from 0 to 3, XY' is a fragmentable electron donor moiety wherein:
1) X is an electron donor group
2) Y' is a leaving proton H or a leaving group Y
3) X—Y' has an oxidation potential between 0 and about 1.4 V
4) the oxidized form of X—Y' undergoes a bond cleavage reaction to give the radical X• and the leaving fragment Y'; and
5) the radical X• has an oxidation potential $\leq -0.7$V.

33. A photographic element comprising at least one silver halide emulsion layer in which the silver halide is sensitized with a protected fragmentable electron donor compound represented by formula:

| ID | Structure |
|---|---|
| i | Z-(L-X-Y'-(t)$_m$-Δ)$_k$ |
| ii | Z—(L—X—Y')$_k$ with (t)$_{\overline{m}}$—Δ branch from X |
| iii | Z—(L—X—Y'—(t)$_{\overline{m}}$—Δ)$_k$ with (t)$_{\overline{m}}$—Δ branch from X |
| iv | A-(L-X-Y'-(t)$_m$-Δ)$_k$ |
| v | A—(L—X—Y')$_k$ with (t)$_{\overline{m}}$—Δ branch from X |
| vi | A—(L—X—Y'—(t)$_{\overline{m}}$—Δ)$_k$ with (t)$_{\overline{m}}$—Δ branch from X |
| vii | (A-L)$_k$-X-Y'-(t)$_m$-Δ |
| viii | (A—L)$_k$—X—Y' with (t)$_{\overline{m}}$—Δ branch from X |
| ix | (A—L)$_k$—X—Y'—(t)$_{\overline{m}}$—Δ with (t)$_{\overline{m}}$—Δ branch from X |
| x | Q-X-Y'-(t)$_m$-Δ |
| xi | Q—X—Y' with (t)$_{\overline{m}}$—Δ branch from X |
| xii | Q—X—Y'—(t)$_{\overline{m}}$—Δ with (t)$_{\overline{m}}$—Δ branch from X |
| xiii | A-(X-Y'-(t)$_m$-Δ)$_k$ |
| xiv | A—(X—Y')$_k$ with (t)$_{\overline{m}}$—Δ branch from X |
| xv | A—(X—Y'—(t)$_{\overline{m}}$—Δ)$_k$ with (t)$_{\overline{m}}$—Δ branch from X |
| xvi | (A)$_k$-X-Y'-(t)$_m$-Δ |
| xvii | (A)$_k$—X—Y' with (t)$_{\overline{m}}$—Δ branch from X |
| xviii | (A)$_k$—X—Y'—(t)$_{\overline{m}}$—Δ with (t)$_{\overline{m}}$—Δ branch from X |
| xix | Z-(X-Y'-(t)$_m$-Δ)$_k$ |
| xx | Z—(X—Y')$_k$ with (t)$_{\overline{m}}$—Δ branch from X |
| xxi | Z—(X—Y'—(t)$_{\overline{m}}$—Δ)$_k$ with (t)$_{\overline{m}}$—Δ branch from X |
| xxii | (Z)$_k$-X-Y'-(t)$_m$-Δ |
| xxiii | (Z)$_k$—X—Y' with (t)$_{\overline{m}}$—Δ branch from X |
| xxiv | (Z)$_k$—X—Y'—(t)$_{\overline{m}}$—Δ with (t)$_{\overline{m}}$—Δ branch from X | wherein Δ is a protective group that is eliminated during development of the photographic element, t is a timing group, m is an integer from 0 to 3, and X—Y' is a fragmentable electron donor moiety in which X is an electron donor group and Y' is a leaving proton H or a leaving group Y, with the proviso that if Y' is a proton, a base, β$^-$, is present in the emulsion or is covalently linked directly or indirectly to X, and wherein:

1) X—Y' has an oxidation potential between 0 and about 1.4 V;
2) the oxidized form of X—Y' undergoes a bond cleavage reaction to give the radical X$^\bullet$ and the leaving fragment Y'; and
3) the radical X$^\bullet$ has an oxidation potential $\leq -0.7$V;

Z is a light absorbing group;
k is 1 or 2;
A is a silver halide adsorptive group;
L represents a linking group containing at least one C, N, S, P or O atom; and
Q represents the atoms necessary to form a chromophore comprising an amidinium-ion, a carboxyl-ion or dipolar-amidic chromophoric system when conjugated with X—Y'.

34. A photographic element according to claim 33, wherein the protected fragmentable electron donor compound is of the formula:

| ID | Structure |
|---|---|
| i | Z-(L-X-Y'-(t)$_m$-Δ)$_k$ |
| ii | Z—(L—X—Y')$_k$ with (t)$_{\overline{m}}$—Δ branch from X |
| iii | Z—(L—X—Y'—(t)$_{\overline{m}}$—Δ)$_k$ with (t)$_{\overline{m}}$—Δ branch from X |
| xix | Z-(X-Y'-(t)$_m$-Δ)$_k$ |
| xx | Z—(X—Y')$_k$ with (t)$_{\overline{m}}$—Δ branch from X |
| xxi | Z—(X—Y'—(t)$_{\overline{m}}$—Δ)$_k$ with (t)$_{\overline{m}}$—Δ branch from X |
| xxii | (Z)$_k$-X-Y'-(t)$_m$-Δ |
| xxiii | (Z)$_k$—X—Y' with (t)$_{\overline{m}}$—Δ branch from X |

-continued

| ID | Structure |
|---|---|
| xxiv | or $(Z)_k$—X—Y'—$(t)_{\overline{m}}$—Δ<br>              │<br>              $(t)_{\overline{m}}$—Δ | wherein Z is derived from a cyanine dye, complex cyanine dye, merocyanine dye, complex merocyanine dye, homopolar cyanine dye, styryl dye, oxonol dye, hemioxonol dye, or hemicyanine dye.

35. A photographic element according to claim 33, wherein the protected fragmentable electron donor compound is of the formula:

| | |
|---|---|
| iv | A-(L-X-Y'-$(t)_m$-Δ)$_k$ |
| v | A—(L—X—Y')$_k$<br>           │<br>           $(t)_{\overline{m}}$—Δ |
| vi | A—(L—X—Y'—$(t)_{\overline{m}}$—Δ)$_k$<br>           │<br>           $(t)_{\overline{m}}$—Δ |
| vii | (A-L)$_k$-X-Y'-$(t)_m$-Δ |
| viii | (A—L)$_k$—X—Y'<br>            │<br>            $(t)_{\overline{m}}$—Δ |
| ix | (A—L)$_k$—X—Y'—$(t)_{\overline{m}}$—Δ<br>            │<br>            $(t)_{\overline{m}}$—Δ |
| xiii | A-(X-Y'-$(t)_m$-Δ)$_k$ |
| xiv | A—(X—Y')$_k$<br>          │<br>          $(t)_{\overline{m}}$—Δ |
| xv | A—(X—Y'—$(t)_{\overline{m}}$—Δ)$_k$<br>           │<br>           $(t)_{\overline{m}}$—Δ |
| xvi | (A)$_k$-X-Y'-$(t)_m$-Δ |
| xvii | (A)$_k$—X—Y'<br>          │<br>          $(t)_{\overline{m}}$—Δ |
| xviii | (A)$_k$—X—Y'—$(t)_{\overline{m}}$—Δ<br>           │<br>           $(t)_{\overline{m}}$—Δ | wherein: A is a silver-ion ligand moiety or a cationic surfactant moiety.

36. A photographic element according to claim 35, wherein A is selected from the group consisting of: i) sulfur acids and their Se and Te analogs, ii) nitrogen acids, iii) thioethers and their Se and Te analogs, iv) phosphines, v) thionamides, selenamides, and telluramides, and vi) carbon acids.

37. A photographic element according to claim 33, wherein the protected fragmentable electron donor compound is of the formula:

| | |
|---|---|
| x | Q-X-Y'-$(t)_m$-Δ |
| xi | Q—X—Y'<br>         │<br>         $(t)_{\overline{m}}$—Δ |
| xii | Q—X—Y'—$(t)_{\overline{m}}$—Δ<br>         │<br>         $(t)_{\overline{m}}$—Δ | wherein Q represents a chromophoric system comprising a cyanine, complex cyanine, hemicyanine, merocyanine, or complex merocyanine dye.

\* \* \* \* \*